(12) United States Patent
Furuya et al.

(10) Patent No.: US 9,835,543 B2
(45) Date of Patent: *Dec. 5, 2017

(54) PARTICLE DETECTOR

(71) Applicant: Azbil Corporation, Chiyoda-ku (JP)

(72) Inventors: Masashi Furuya, Chiyoda-ku (JP); Daisuke Obara, Chiyoda-ku (JP)

(73) Assignee: AZBIL CORPORATION, Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/047,389

(22) Filed: Feb. 18, 2016

(65) Prior Publication Data

US 2016/0238512 A1 Aug. 18, 2016

(30) Foreign Application Priority Data

Feb. 18, 2015 (JP) ................................. 2015-029997

(51) Int. Cl.
| | |
|---|---|
| *G21K 7/00* | (2006.01) |
| *G01N 15/14* | (2006.01) |
| *G01N 15/10* | (2006.01) |
| *G01N 21/53* | (2006.01) |
| *G01N 21/64* | (2006.01) |

(52) U.S. Cl.
CPC ..... *G01N 15/1436* (2013.01); *G01N 15/1459* (2013.01); *G01N 21/53* (2013.01); *G01N 2015/1006* (2013.01); *G01N 2021/6469* (2013.01)

(58) Field of Classification Search
CPC ........... G01N 15/1459; G01N 15/1434; G01N 15/1436; G01N 21/49; G01N 15/1404; G01N 21/53; G01N 2015/0238; G01N 2021/5957; G01N 2021/6439; G01N 21/64; G01N 2201/0612; G01N 2201/062
USPC ......................................................... 250/306
See application file for complete search history.

(56) References Cited

U.S. PATENT DOCUMENTS

| | | | | |
|---|---|---|---|---|
| 4,273,443 A | * | 6/1981 | Hogg | G01N 15/1436 250/574 |
| 5,412,466 A | * | 5/1995 | Ogino | G01N 15/1404 356/246 |
| 5,436,717 A | * | 7/1995 | Ogino | G01N 15/1404 250/458.1 |

(Continued)

FOREIGN PATENT DOCUMENTS

| | | | |
|---|---|---|---|
| JP | | 4540509 B2 | 9/2010 |
| WO | WO 2010/080642 A1 | | 7/2010 |

*Primary Examiner* — Taeho Jo
(74) *Attorney, Agent, or Firm* — Oblon, McClelland, Maier & Neustadt, L.L.P.

(57) ABSTRACT

A particle detector that includes an inspection light source that irradiates a flow cell with inspection light, the flow cell that allows a fluid containing a particle to flow therethrough, the flow cell including a semispherical reflective film that reflects reaction light generated by the particle irradiated with the inspection light, and a semispherical lens portion through which the reaction light reflected by the semispherical reflective film passes, an elliptical mirror that has a first focus at a position of the flow cell, and that reflects the reaction light having passed through the semispherical lens portion of the flow cell, and an optical detector that is disposed at a second focus of the elliptical mirror and that detects the reaction light reflected by the elliptical mirror.

10 Claims, 30 Drawing Sheets

(56) References Cited

U.S. PATENT DOCUMENTS

| | | | | |
|---|---|---|---|---|
| 5,825,477 A * | 10/1998 | Furuie | G01N 15/0227 | 356/335 |
| 6,104,483 A * | 8/2000 | Sebok | G01N 21/05 | 356/244 |
| 6,184,517 B1 * | 2/2001 | Sawada | G01N 15/0205 | 250/222.2 |
| 6,482,652 B2 * | 11/2002 | Furlong | B07C 5/3425 | 209/3.1 |
| 9,267,887 B2 * | 2/2016 | Kanomata | G01N 21/64 | |
| 2004/0011975 A1 * | 1/2004 | Nicoli | G01N 15/0227 | 250/574 |
| 2005/0068536 A1 * | 3/2005 | Schwabe | B01L 3/502715 | 356/436 |
| 2006/0001875 A1 * | 1/2006 | Christodoulou | G01N 15/1459 | 356/342 |
| 2006/0132770 A1 * | 6/2006 | Girvin | G01N 15/1459 | 356/338 |
| 2009/0029870 A1 * | 1/2009 | Ward | G01N 15/1404 | 506/9 |
| 2011/0066382 A1 * | 3/2011 | Adams | G01N 15/147 | 702/19 |
| 2011/0127444 A1 * | 6/2011 | Ozasa | G01N 15/147 | 250/458.1 |
| 2011/0235030 A1 * | 9/2011 | Champseix | G01N 15/1209 | 356/243.2 |
| 2011/0291025 A1 * | 12/2011 | Fortin | G01N 15/1436 | 250/458.1 |
| 2012/0196356 A1 * | 8/2012 | Wagner | C12N 5/0612 | 435/288.7 |
| 2012/0257192 A1 * | 10/2012 | Jiang | G01N 21/6486 | 356/73 |
| 2013/0161243 A1 * | 6/2013 | Kanomata | G01N 30/74 | 210/85 |
| 2014/0030696 A1 * | 1/2014 | Luscher | G01N 15/1404 | 435/3 |
| 2014/0234865 A1 * | 8/2014 | Gabriel | G01N 33/5008 | 435/7.21 |
| 2015/0115174 A1 * | 4/2015 | Chen | G01N 15/1459 | 250/458.1 |
| 2015/0233812 A1 * | 8/2015 | Yan | G01N 15/1434 | 250/214.1 |
| 2016/0252443 A1 * | 9/2016 | Spriggs | G01N 15/1456 | 356/336 |

* cited by examiner

PARTICLE DETECTOR

CROSS-REFERENCE TO RELATED APPLICATIONS

This application claims priority to Japanese Application No. 2015-029997, filed Feb. 18, 2015, the entire contents of which are incorporated herein by reference.

BACKGROUND

1. Field of the Disclosure

The present disclosure relates to a detection technique and a particle detector.

2. Description of the Related Art

Flow cells that allow a fluid as a sample to flow therethrough are used for particle detectors including, for example, flow cytometers and microorganism detectors. Such a flow cell is transparent, and when a fluid flowing through the flow cell is irradiated with light, particles contained in the fluid emit fluorescence and scattered light. The fluorescence and the scattered light are condensed by a lens disposed next to the flow cell so as to be detected (see, for example, Japanese Patent No. 4540509, U.S. Patent Application Publication No. 2012/0140221, U.S. Pat. No. 7,355,706, and International Publication No. 2010/080642). The number and the type of the particles contained in the fluid can be identified by the number of times of detection, detected intensity, a detected wavelength, and so forth of the fluorescence and the scattered light. For example, whether or not the particles are a biological particle, whether or not the particles are resin, whether or not the particles are an air bubble, and so forth can be determined. There also is a case in which an airflow is irradiated with light so as to detect particles contained in the airflow without using the flow cell (for example, see U.S. Patent Application Publication No. 2013/0077087).

SUMMARY

According to one aspect of the disclosure, there is provided a particle detector that includes an inspection light source configured to irradiate a flow cell with inspection light, the flow cell configured to allow a fluid containing a particle to flow therethrough, the flow cell including a semispherical reflective film that reflects reaction light generated by the particle irradiated with the inspection light, and a semispherical lens portion through which the reaction light reflected by the semispherical reflective film passes, an elliptical mirror that has a first focus at a position of the flow cell, and that is configured to reflect the reaction light having passed through the semispherical lens portion of the flow cell, and an optical detector disposed at a second focus of the elliptical mirror, the optical detector being configured to detect the reaction light reflected by the elliptical mirror.

DESCRIPTION OF THE EMBODIMENTS

Figure 1:
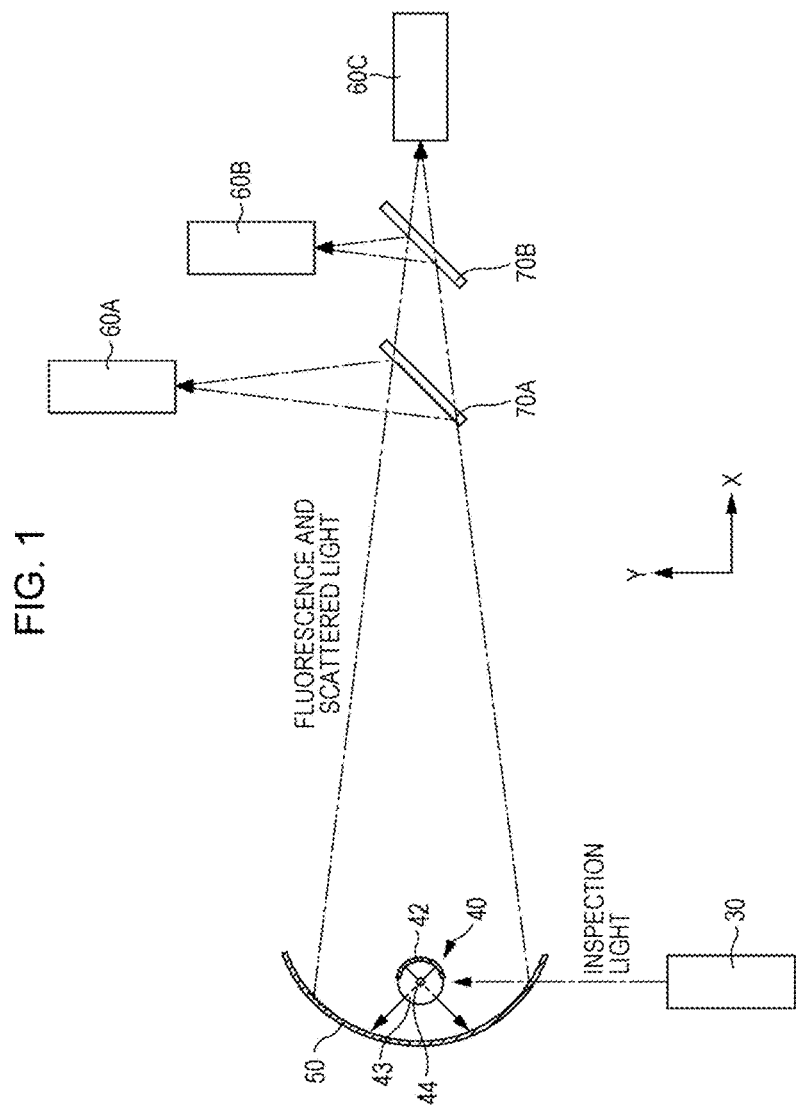
FIG. 1 is a schematic view of a particle detector according to a first embodiment of the present disclosure.

The inventors conducted devoted investigation and finally found that, since the fluorescence and the scattered light generated by the particles in the flow cell are omnidirectionally emitted from the particles, the numerical aperture of the lens that condenses the fluorescence and the scattered light needs to be high. However, a high-numerical-aperture lens needs a complex optical system. Thus, there is a problem in that the production cost of the particle detector increases. Furthermore, a high-numerical-aperture lens has a short focal length. Thus, there is a problem in that the flexibility in arrangement of the optical system including the lens with respect to the flow cell reduces- Furthermore, there is a problem in that a lens with a numerical aperture of 1.0 cannot actually exist. Accordingly, one of objects of the present disclosure is that a particle detector that can efficiently detect particles without a high-numerical-aperture lens arranged next to a flow cell can be provided.

According to an aspect of the present disclosure, a particle detector includes (a) an inspection light source that emits inspection light, (b) a flow cell that is irradiated with the inspection light, that allows a fluid containing a particle to flow through the flow cell, and that includes a semispherical reflective film which reflects reaction light generated by the particle irradiated with the inspection light and a semispherical lens portion through which the reaction light reflected by the semispherical reflective film passes, (c) an elliptical mirror that has a first focus at a position of the flow cell and that, reflects the reaction light having passed through the semispherical lens portion of the flow cell, and (d) an optical detector that is disposed at a second focus of the elliptical mirror and that detects the reaction light reflected by the elliptical mirror.

The reaction light may be fluorescence, scattered light, or both the fluorescence and the scattered light. The elliptical mirror may have a cut in a traveling direction of the inspection light.

The flow cell may include a spherical member that is transparent and that has a through hole which allows the fluid to flow through the through hole, the semispherical reflective film may cover part of the spherical member, and part of the spherical member not covered by the semispherical reflective film may function as the semispherical lens portion. Here, a sectional shape of the through hole provided in the spherical member may be circular.

The flow cell may include (a) a plate-shaped member that is transparent, that includes a first main surface, a second main surface which faces the first main surface, and one and another side surfaces which are perpendicular to the first main surface and the second main surface, and that has a through hole which penetrates through the plate-shaped member from the one side surface to the other side surface, (b) a first semispherical member that is transparent and that is disposed on the first main surface of the plate-shaped member, and (c) a second semispherical member that is transparent and that is disposed on the second main surface of the plate-shaped member. (d) The semispherical reflective film may cover the first semispherical member that is transparent, and (e) the second semispherical member may function as the semispherical lens portion. Here, a sectional shape of the through hole provided in the plate shaped member may be circular.

Alternatively, the flow cell may include (a) a plate-shaped member that is transparent, that includes a first-main surface and a second main surface which faces the first main surface, and that has a first through hole which penetrates through the plate-shaped member from the first main surface to the second main surface, (b) a first semispherical member that is transparent, that has a second through hole, and that is disposed on the first main surface of the plate-shaped member such that the first through hole and the second through hole communicate with each other, and (c) a second semispherical member that is transparent, that has a third through hole, and that is disposed on the second main surface of the plate-shaped member such that the first through hole and the third through hole communicate with each other. (d) The semispherical reflective film may cover the first semispherical member that is transparent, and (e) the second semispherical member may function as the semispherical lens portion.

Here, sectional shapes of the first through hole, the second through hole, and the third through hole may be circular. Smoothnesses of inner walls of the second through hole and the third through hole may be lower than a smoothness of an inner wall of the first through hole. Diameters of the second through hole and the third through hole may be larger than a diameter of the first through hole. Transparencies of the first semispherical member and the second semispherical member may be lower than a transparency of the plate shaped member. The plate-shaped member may be formed of silica glass, the first semispherical member may be formed of a different material from the silica glass, and the second semispherical member may be formed of a different material from the silica glass. The plate-shaped member, the first semispherical member, and the second semispherical member may be joined to one another by optical contact.

According to the present disclosure, the particle detector that can efficiently detect the particles can be provided.

Embodiments of the present disclosure will be described below. In the drawings referred to below, the same or similar elements are denoted by the same or similar signs. Also, the drawings are schematic. Accordingly, it should be understood that specific dimensions and the like are determined in view of the following description. In addition, of course, the relationships or the ratios of the dimensions may differ between the drawings.

FIRST EMBODIMENT

A particle detector according to a first embodiment of the present disclosure includes, as illustrated in FIG. 1, an inspection light source 30, a flow cell 40, an elliptical mirror 50, and optical detectors 60A, 60B, and 60C. The inspection light source 30 emits inspection light. The flow cell 40 is irradiated with the inspection light, allows a fluid containing particles to flow therethrough, and includes a semispherical reflective film 42 and a semispherical lens portion 43. The semispherical reflective film 42 reflects reaction light generated by the particles irradiated with the inspection light. The reaction light reflected by the semispherical reflective film 42 passes through the semispherical lens portion 43. The elliptical mirror 50 has a first focus at the position of the flow cell 40 and reflects the reaction light having passed through the semispherical lens portion 43 of the flow cell 40. The optical detectors 60A, 60B, and 60C are disposed at a second focus of the elliptical mirror 50 and detect the reaction light reflected by the elliptical mirror 50. Here, the fluid is, for example, a liquid. Also, the reaction light refers to at least one of fluorescence and scattered light.

Figure 2:
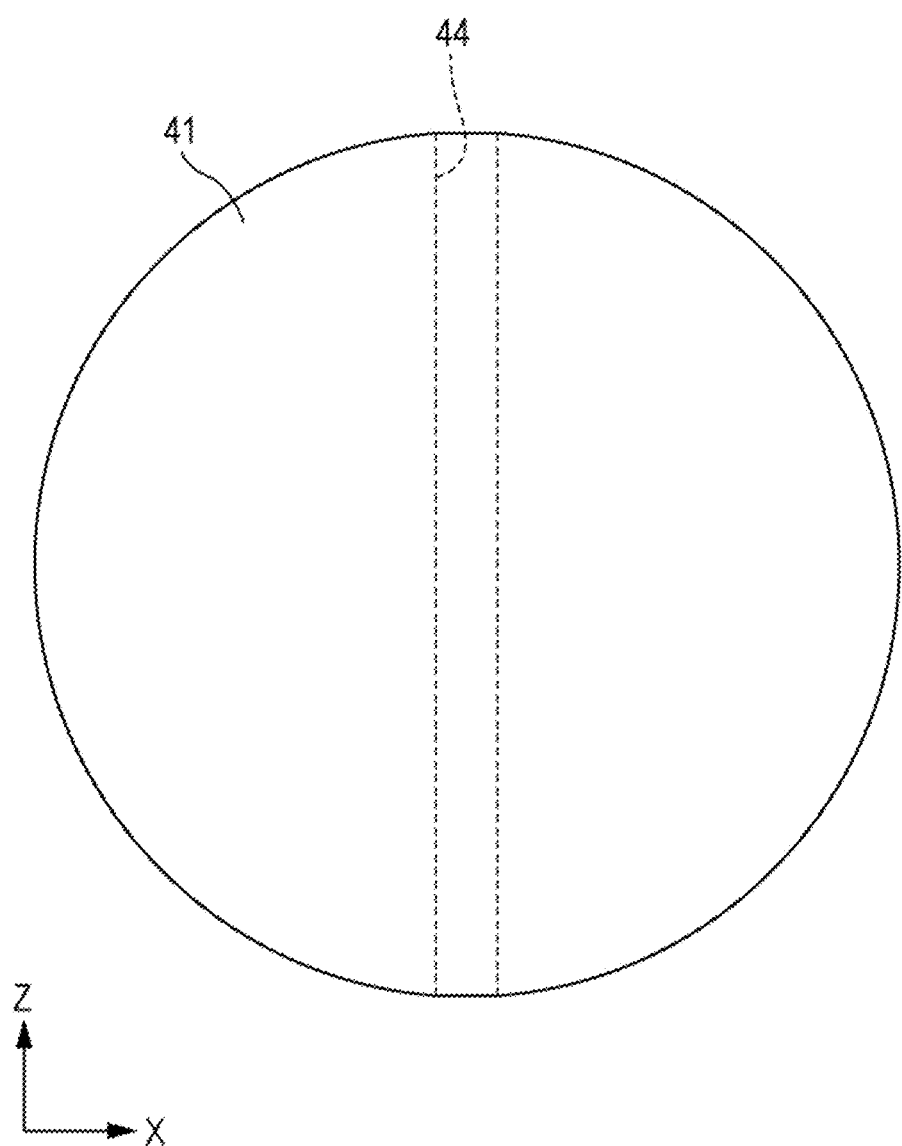
FIG. 2 is a schematic view of a spherical member included in a flow cell according to the first embodiment of the present disclosure.

The flow cell 40 includes, as illustrated in FIG. 2, a transparent spherical member 41 having a through hole 44 which allows the fluid containing particles to be inspected to flow therethrough. A surface of the transparent spherical member 41 and an inner wall of the through hole 44 are, for example, ground. The through hole 44 passes through, for example, the center of the spherical member 41. The through hole 44 has, for example, a circular sectional shape when seen in the extending direction thereof. By forming the through hole 44 to have a circular sectional shape so that no angle is formed in the inner wall, accumulation of bubbles and adhesion of contamination inside the through hole 44 can be suppressed. The extending direction of the through hole 44 is perpendicular to the traveling direction of the inspection light and perpendicular to a major axis direction of the elliptical mirror 50. The diameter of the through hole 44 is, although it is not limited to this, for example, less than 1 mm. The spherical member 41 is formed of, for example, silica glass.

Figure 3:
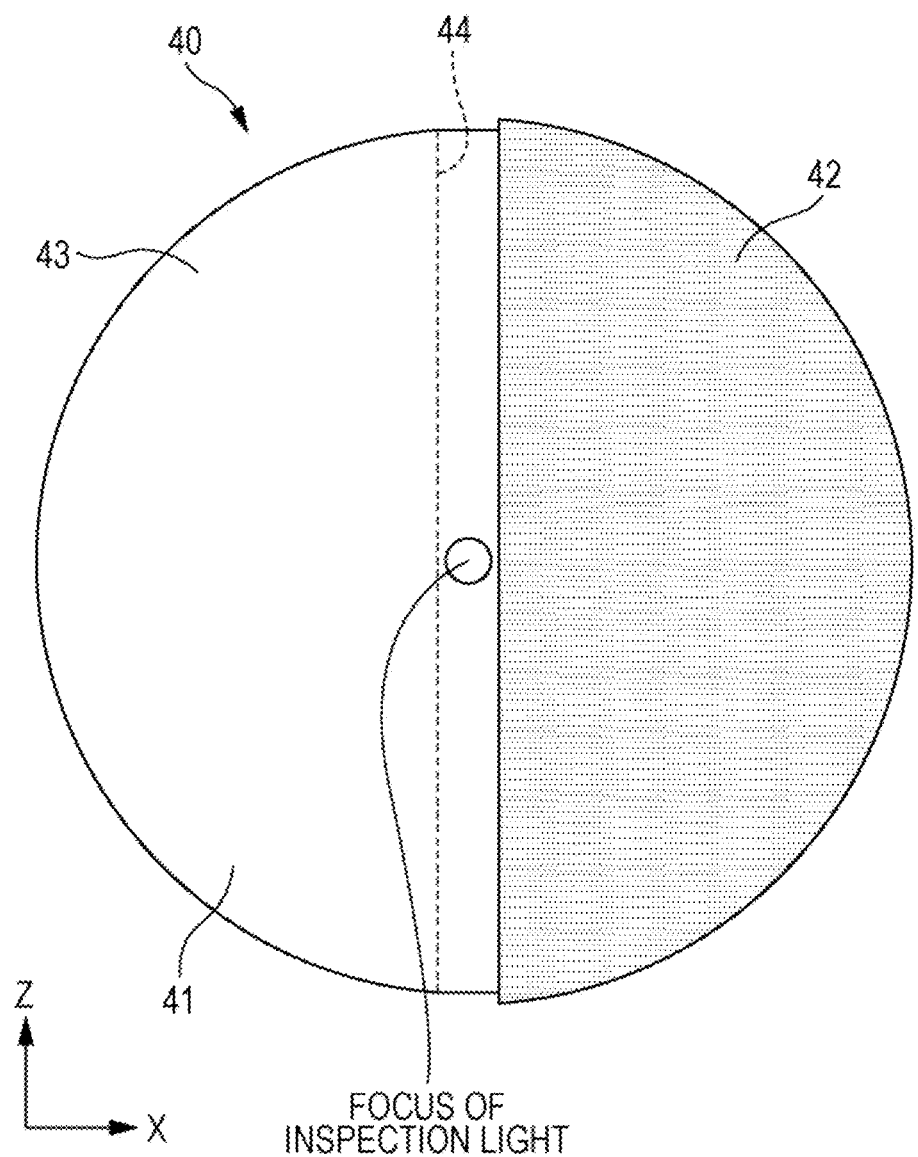
FIG. 3 is a side view of the flow cell according to the first embodiment of the present disclosure.
Figure 4:
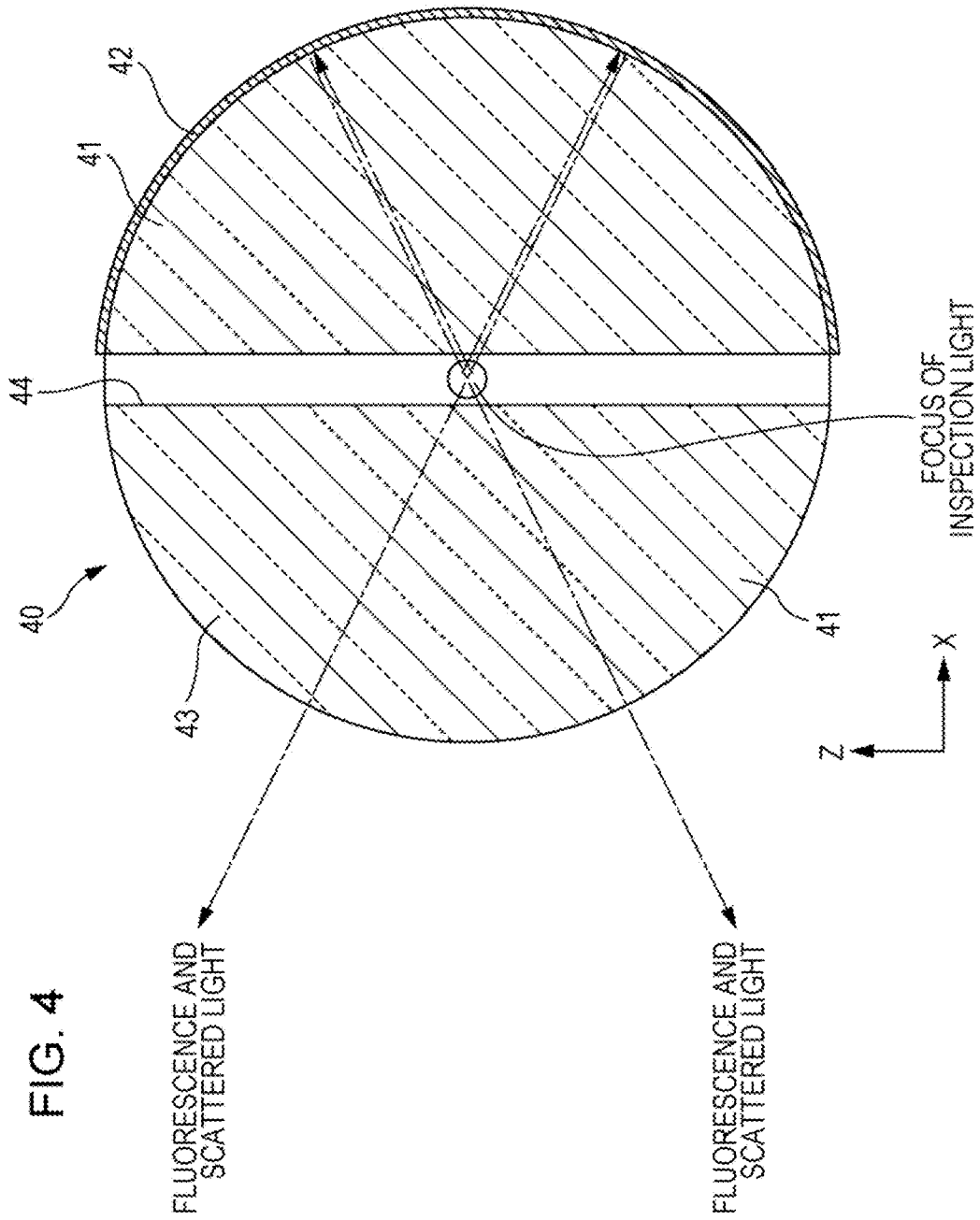
FIG. 4 is a sectional view of the flow cell according to the first embodiment of the present disclosure.

As illustrated in FIGS. 3 and 4, the semispherical reflective film 42 covers part of the spherical member 41, for example, covers about a half of the spherical member 41 divided by the through hole 44. The semispherical reflective film 42 is, for example, a vapor deposited film and formed of metal or the like. Alternatively, the semispherical reflective film 42 may be a dielectric multilayer film. Part of the spherical member 41 not covered by the semispherical reflective film 42 functions as the semispherical lens portion 43. The semispherical reflective film 42 and the semispherical lens portion 43 face each other.

As illustrated in FIG. 1, the flow cell 40 is disposed such that a convex portion of the semispherical lens portion 43 and the concave portion of the semispherical reflective film 42 face the elliptical mirror 50. Furthermore, the flow cell 40 is disposed such that the center of the flow cell 40 where the through hole 44 passes is coincident with the first focus of the elliptical mirror 50.

The particles contained in the fluid flowing through the flow cell 40 include, for example, biological substances including microorganisms and the like, cells, chemical substances, dust such as pieces of refuse, motes, and dirt. Examples of the microorganisms include bacteria and fungi. Examples of the bacteria include Gram-negative bacteria and Gram-positive bacteria. Examples of the Gram-negative bacteria include colon bacilli. Examples of the Gram-positive bacteria include *Staphylococcus epidermidis*, *Bacillus subtilis*, micrococci, and corynebacteria. Examples of fungi include *Aspergillus* such as black patches. Despite the above description, the microorganisms are not limited to the above-described microorganisms.

In the case where fluorescent particles such as microorganisms are contained in the fluid, the particles emit fluorescence when the particles are irradiated with excitation light. For example, riboflavin, flavin mononucleotide (FMN), flavin adenine dinucleotide (FAD), nicotinamide adenine dinucleotide phosphate (NAD (P) H), pyridoxamine, pyridoxal-5'-phosphate, pyridoxine, tryptophan, tyrosine, phenylalanine, and so forth contained in the microorganisms emit fluorescence.

The excitation light as the inspection light for detecting the fluorescent particles flowing through the flow cell 40 is radiated from the inspection light source 30 illustrated in FIG. 1 so as to be focused on, for example, the center of the spherical flow cell 40. A light emitting diode (LED) or a laser may be used as the inspection light source 30. The wavelength of the inspection light is, for example, from 250 to 550 nm. The inspection light may be visible light or ultraviolet light. When the inspection light is visible light, the wavelength of the inspection light is, for example, in a range from 400 to 550 nm. An example of such a wavelength is 405 nm. When the inspection light is ultraviolet light, the wavelength of the inspection light is, for example, in a range from 300 to 380 nm. An example of such a wavelength is 340 nm, However, the wavelength of the inspection light is not limited to any of the above-described wavelengths.

The fluorescent particles irradiated with the excitation light in the through hole 44 that serves as an inspection region emit fluorescence. Furthermore, scattered light is generated due to, for example, Mie scattering with the fluorescent particles and non-fluorescent particles irradiated with the excitation light. The fluorescence and the scattered light as the reaction light generated by the particles irradiated with light are omnidirectionally emitted from the particles.

The fluorescence and the scattered light having traveled toward the semispherical lens portion 43 of the flow cell 40 illustrated in FIG. 4 exit through the surface of the semispherical lens portion 43 and reach the elliptical mirror 50. In the case where the focus of the inspection light is coincident with the center of the spherical member 41, the fluorescence and the scattered light generated at the focus of the inspection light are perpendicularly or substantially perpendicularly incident upon the surface of the semispherical lens portion 43. Thus, the fluorescence and the scattered light exit through the surface of the semispherical lens portion 43 without or substantially without being refracted at the surface of the semispherical lens portion 43.

The fluorescence and the scattered light having traveled toward the semispherical reflective film 42 of the flow cell 40 are reflected by the semispherical reflective film 42, exit through the surface of the semispherical lens portion 43, and reach the elliptical mirror 50. In the case where the focus of the inspection light is coincident with the center of the spherical member 41, the fluorescence and the scattered light generated at the focus of the inspection light are perpendicularly or substantially perpendicularly incident upon the surface of the semispherical reflective film 42. Thus, the fluorescence and the scattered light are perpendicularly or substantially perpendicularly reflected by the semispherical reflective film 42, pass through the center or a portion near the center of the spherical member 41, and exit through the surface of the semispherical lens portion 43 without or substantially without being refracted at the surface of the semispherical lens portion 43.

The concavity of the elliptical mirror 50 illustrated in FIG. 1 faces the concavity of the semispherical reflective film 42 and the convexity of the semispherical lens portion 43. For example, the elliptical mirror 50 almost surrounds the flow cell 40. The fluorescence and the scattered light having exited through the surface of the semispherical lens portion 43 are reflected by the elliptical mirror 50 and condensed at the second focus of the elliptical mirror 50 behind the flow cell 40. For example, by sufficiently increasing the size of the elliptical mirror 50 compared to the semispherical reflective film 42 of the flow cell 40, efficiency with which the fluorescence and the scattered light are condensed by the elliptical mirror 50 is improved. Wavelength selective reflectors 70A and 70B are disposed between the first and second geometrical foci of the elliptical mirror 50.

The wavelength selective reflector 70A wavelength selectively reflects, for example, the scattered light. The focus of the scattered light reflected by the wavelength selective reflector 70A is optically equivalent to the second geometrical focus of the elliptical mirror 50. The optical detector 60A that detects the scattered light is disposed at the focus of the scattered light reflected by the wavelength selective reflector 70A. A band-pass filter, a long-pass filter, or the like including a dielectric multilayer film or the like may be disposed between the wavelength selective reflector 70A and the optical detector 60A.

The wavelength selective reflector 70B, for example, wavelength selectively reflects the fluorescence of a first wavelength band and allows the fluorescence of a second wavelength band to pass therethrough. The focus of the fluorescence reflected by the wavelength selective reflector 70B is optically equivalent to the second geometrical focus of the elliptical mirror 50. The optical detector 60B that detects the fluorescence of the first wavelength band is disposed at the focus of the fluorescence of the first wavelength band reflected by the wavelength selective reflector 70B. The optical detector 60C that detects the fluorescence of the second wavelength band is disposed at the focus of the fluorescence of the second wavelength band having passed through the wavelength selective reflector 70B. A band-pass filter and a long-pass filter including a dielectric multilayer film or the like, and the like may be disposed between the wavelength selective reflector 70B and the optical detector 60B and between the wavelength selective reflector 70B and the optical detector 60C.

Any of a dichroic mirror, an interference film filter, an optical filter, and so forth may be used as the wavelength selective reflectors 70A and 70B. When the incident angles relative to the wavelength selective reflectors 70A and 70B are 45 degrees in the design, spectral efficiency of the interference film filters tends to increase by setting the distance between the first focus and the second focus of the elliptical mirror 50 so that the incident angles of the scattered light and the fluorescence relative to the wavelength selective reflectors 70A and 70B are from 35 to 55 degrees. However, this is not limiting. Furthermore, when an optical system in which the incident angle is zero degrees in the design includes the band-pass filter and the long-pass filter, it is preferable that the incident angles of the scattered light and the fluorescence relative to the band-pass filter and the long-pass filter be set to ten degrees or less.

With the above-described particle detector according to the first embodiment, the fluorescence and the scattered light having initially traveled to an opposite side to the elliptical mirror 50 can be condensed at the positions of the optical detectors 60A, 60B, and 60C by reflecting the fluorescence and the scattered light toward the elliptical mirror 50 by using the semispherical reflective film 42. Accordingly, the fluorescence and the scattered light that have been initially omnidirectionally emitted from the particles in the flow cell 40 can be condensed with efficiency equal to or higher than that of a lens condensing system and detected.

Furthermore, in the particle detector according to the first embodiment, the size of the semispherical reflective film 42 can be reduced by disposing the semispherical reflective film 42 in the flow cell 40. Accordingly, the area of the shadow of the semispherical reflective film 42 can be reduced and the efficiency with which the fluorescence and the scattered light are condensed is improved. Thus, the weak fluorescence and the scattered light can be efficiently detected without a complex optical system that includes an expensive high-numerical-aperture lens. Furthermore, the particle detector according to the first embodiment does not need a complex optical system. This facilitates production and adjustment of the particle detector.

SECOND EMBODIMENT

Figure 5:
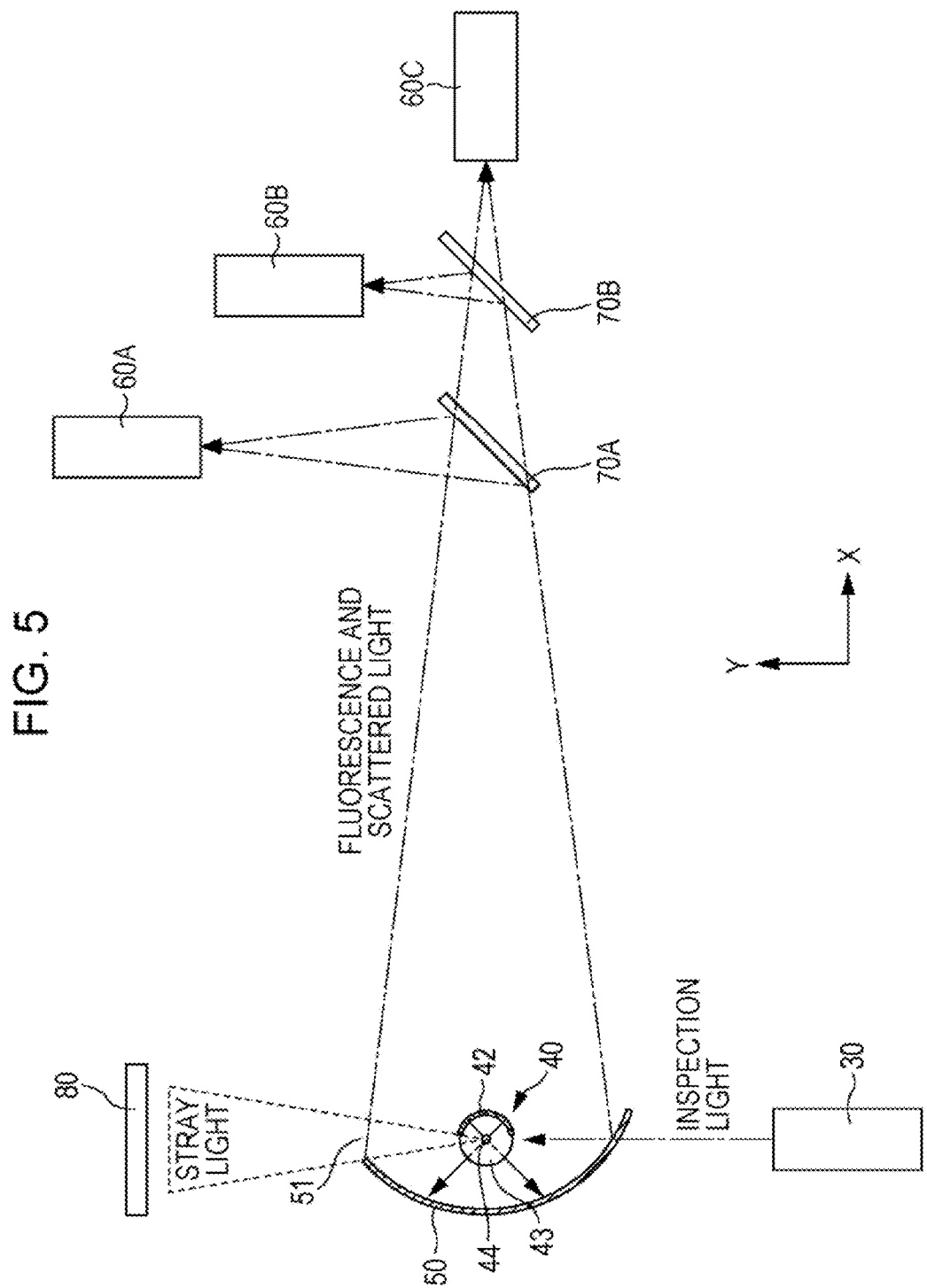
FIG. 5 is a schematic view of a particle detector according to a second embodiment of the present disclosure.

In a particle detector according to a second embodiment of the present disclosure, as illustrated in FIG. 5, a cut 51 is provided in the elliptical mirror 50 in the traveling direction of the inspection light. When the inspection light is radiated to the flow cell 40, the inspection light may scatter at positions such as an outer wall of the flow cell 40 and the inner wall of the through hole 44 and may become stray light. The stray light tends to diverge in a conical shape having a vertex angle of about 30 to 60 degrees from a vertex at positions of the outer wall of the flow cell 40, the inner wall of the through hole 44, and so force irradiated with the inspection light.

Unlike Mie scattering caused with the particles flowing through the through hole 44 of the flow cell 40, the stray light is not needed for detection of the particles. However, when the stray light is reflected by the elliptical mirror 50, the stray light may reach the optical detectors 60A, 60B, and 60C, and accordingly may cause noise.

Thus, by providing the cut 51 at a portion where the elliptical mirror 50 intersects the conical space in which the stray light diverges, the stray light can be prevented from being reflected by the elliptical mirror 50 and reaching the optical detectors 60A, 60B, and 60C. Furthermore, a stray light absorbing member 80 that blocks or attenuates the stray light may be disposed in a traveling direction of the stray light. A cut may also be provided in a portion of the semispherical reflective film 42 where the semispherical reflective film 42 intersects the conical space in which the stray light diverges. Other elements of the particle detector according to the second embodiment are the same as or similar to those of the first embodiment.

THIRD EMBODIMENT

Figure 6:
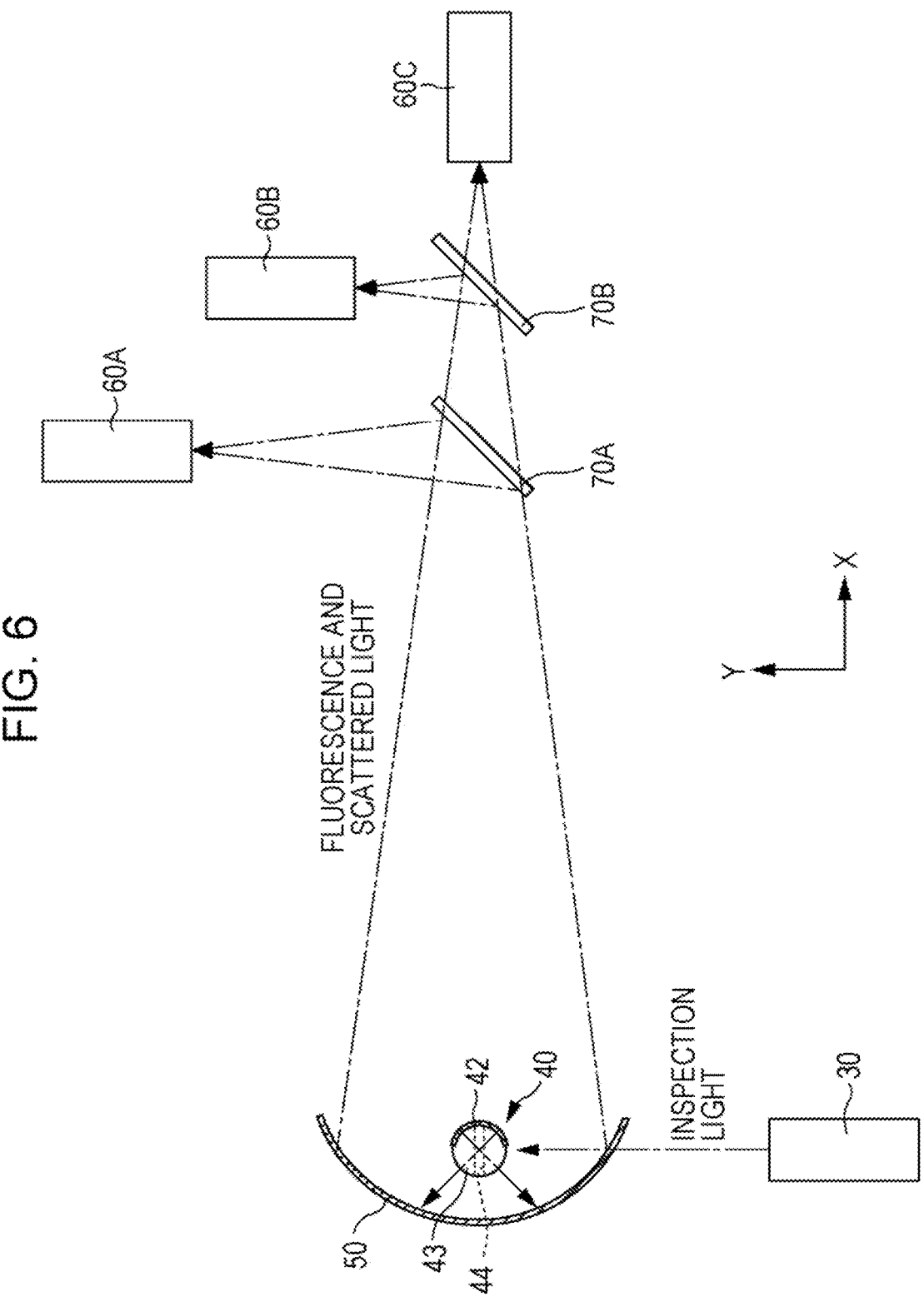
FIG. 6 is a schematic view of a particle detector according to a third embodiment of the present disclosure.

In an example of the first embodiment, as illustrated in FIG. 1, the extending direction of the through hole 44 of the flow cell 40 is perpendicular to the traveling direction of the inspection light and perpendicular to the major axis direction of the elliptical mirror 50. Alternatively, as illustrated in FIG. 6, the extending direction of the through hole 44 of the flow cell 40 may be perpendicular to the traveling direction of the inspection light and parallel to the major axis direction of the elliptical mirror 50.

Figure 7:
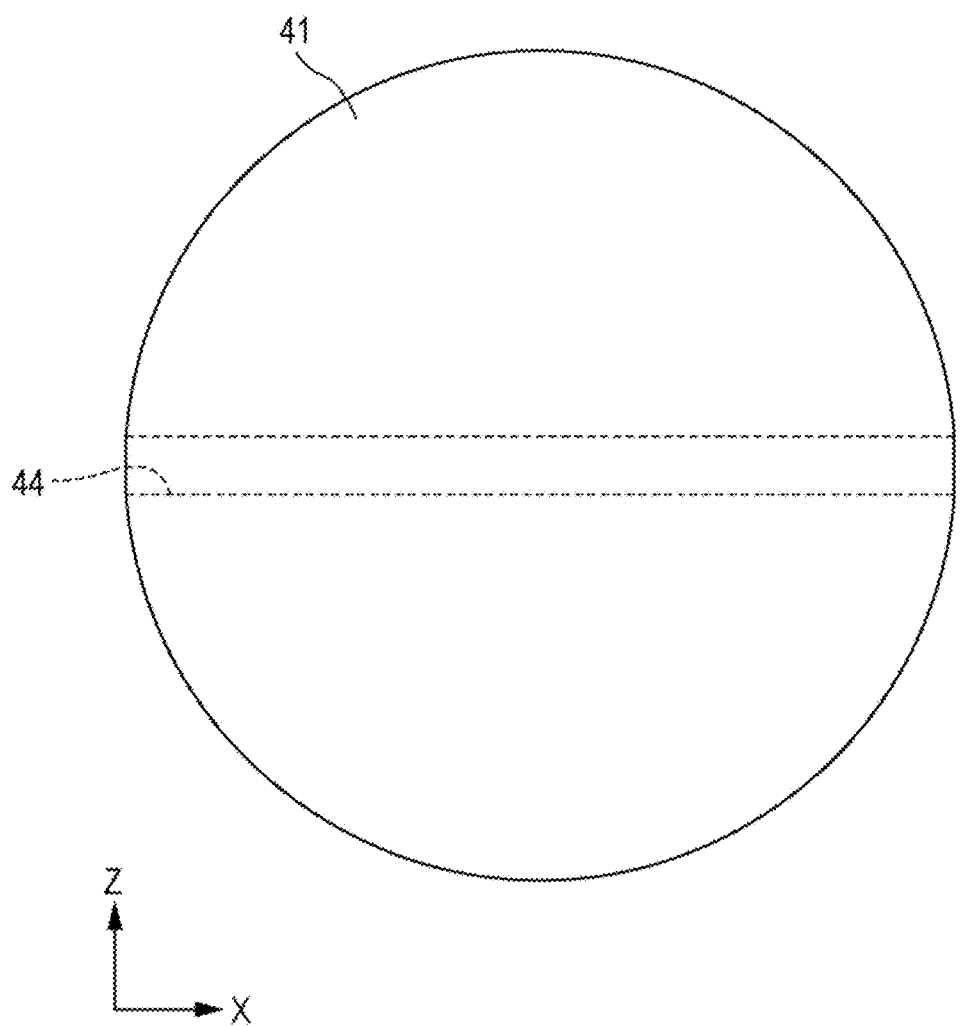
FIG. 7 is a schematic view of a spherical member included in a flow cell according to the third embodiment of the present disclosure.
Figure 8:
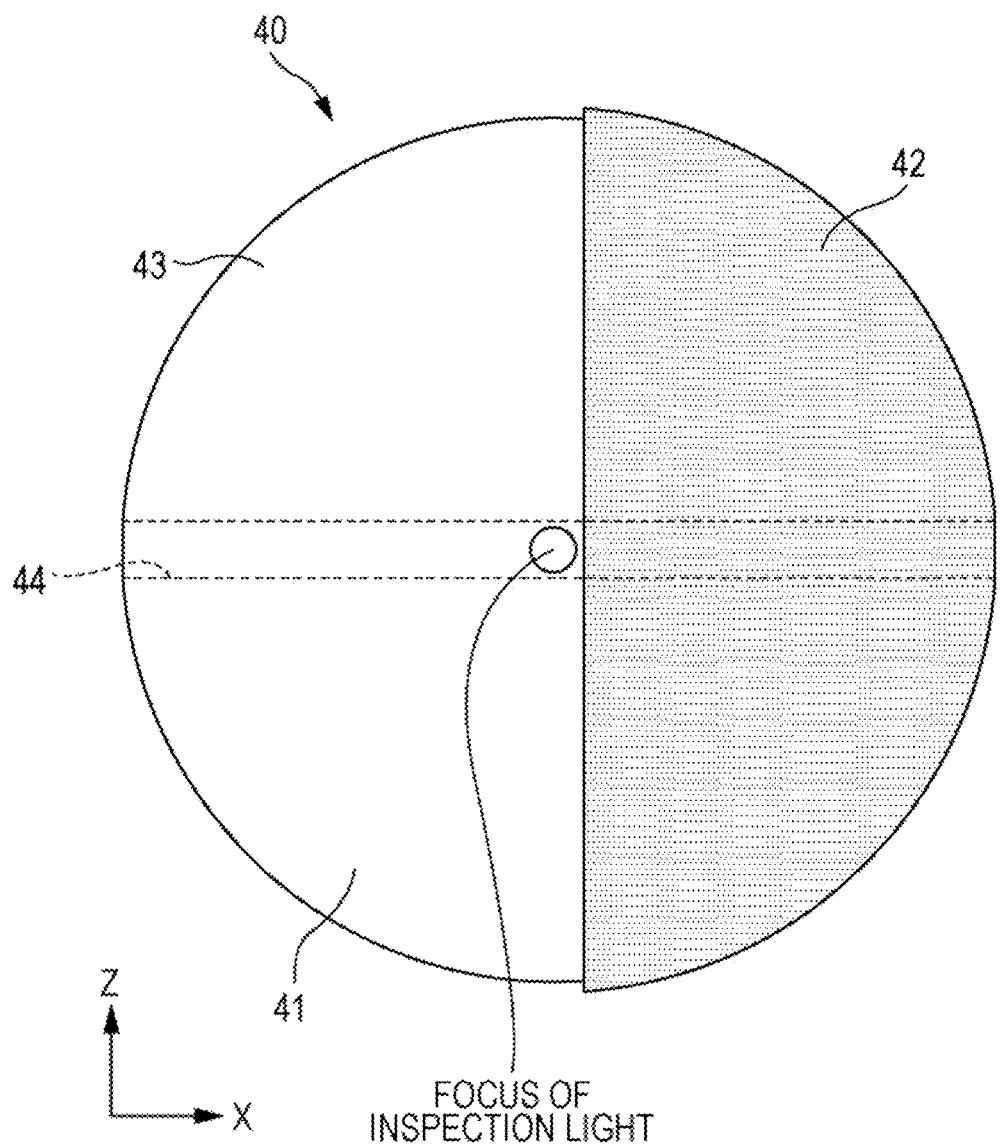
FIG. 8 is a side view of the spherical member included in the flow cell according to the third embodiment of the present disclosure.
Figure 9:
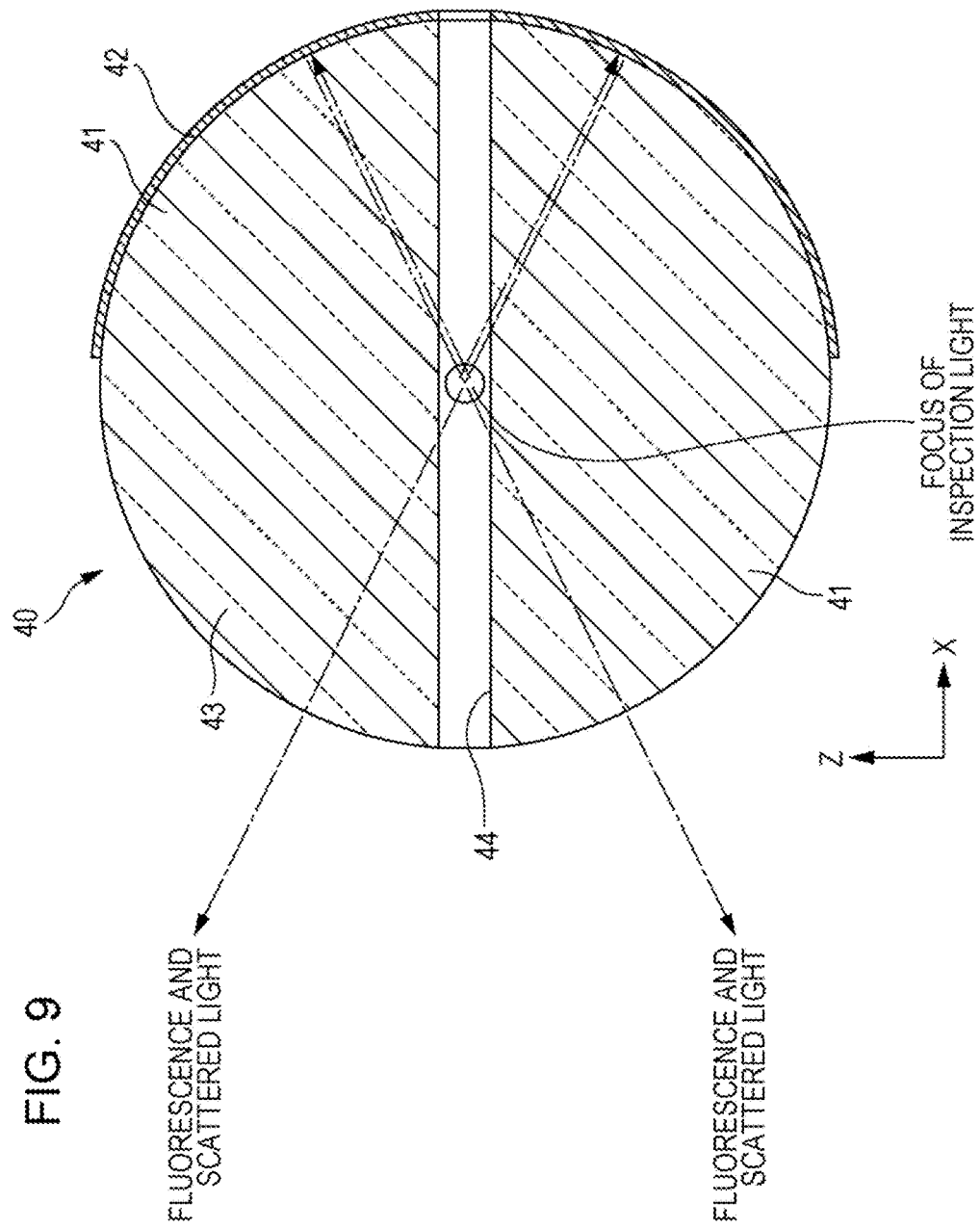
FIG. 9 is a sectional view of the spherical member included in the flow cell according to the third embodiment of the present disclosure.

According to a third embodiment, as illustrated in FIGS. 7 to 9, one of openings of the through hole 44 of the flow cell 40 is provided at the center of a portion of the spherical member 41 covered by the semispherical reflective film 42, and another opening of the through hole 44 is provided at the center of a portion of the spherical member 41 that is not covered by the semispherical reflective film 42 and that functions as the semispherical lens portion 43.

Other elements of a particle detector according to the third embodiment are the same as or similar to those of the first embodiment. In the particle detector according to the third embodiment, since the through hole 44 of the flow cell 40 is coincident with the major axis of the elliptical mirror 50, an effect of shading a channel or the like connected to the through hole 44 from the fluorescence and the scattered light can be suppressed.

FOURTH EMBODIMENT

Figure 10:
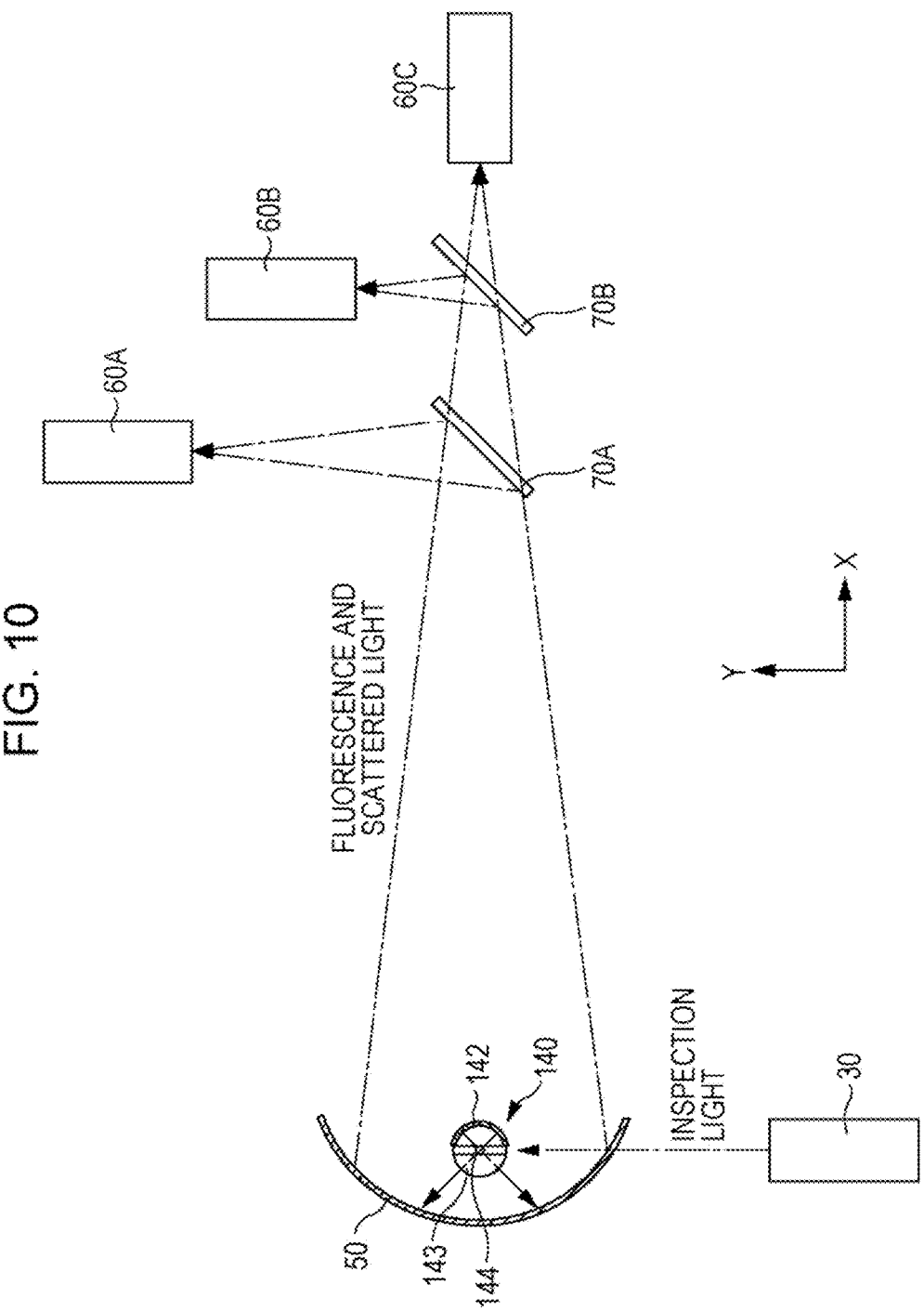
FIG. 10 is a schematic view of a particle detector according to a fourth embodiment of the present disclosure.
Figure 11:
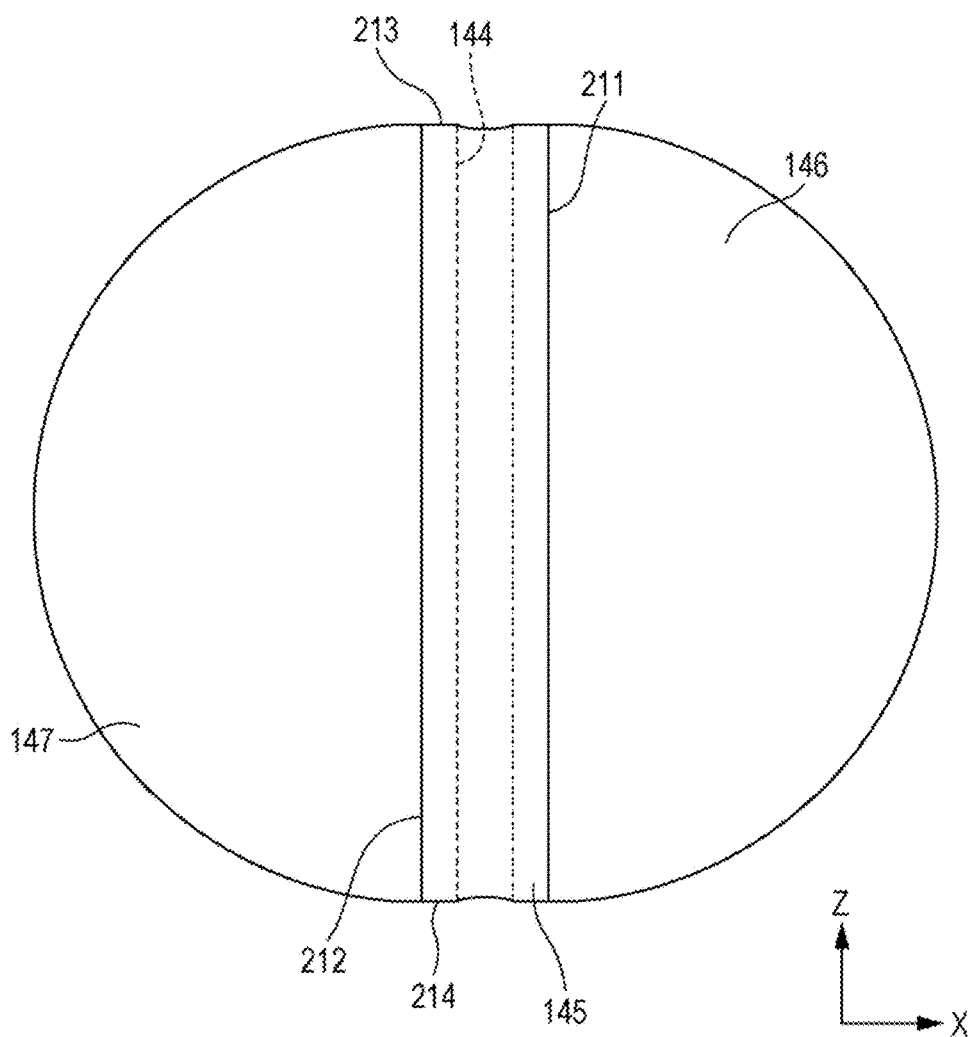
FIG. 11 is a schematic view of a plate-shaped member, a first semispherical member, and a second semispherical member which are included in a flow cell according to the fourth embodiment of the present disclosure.
Figure 12:
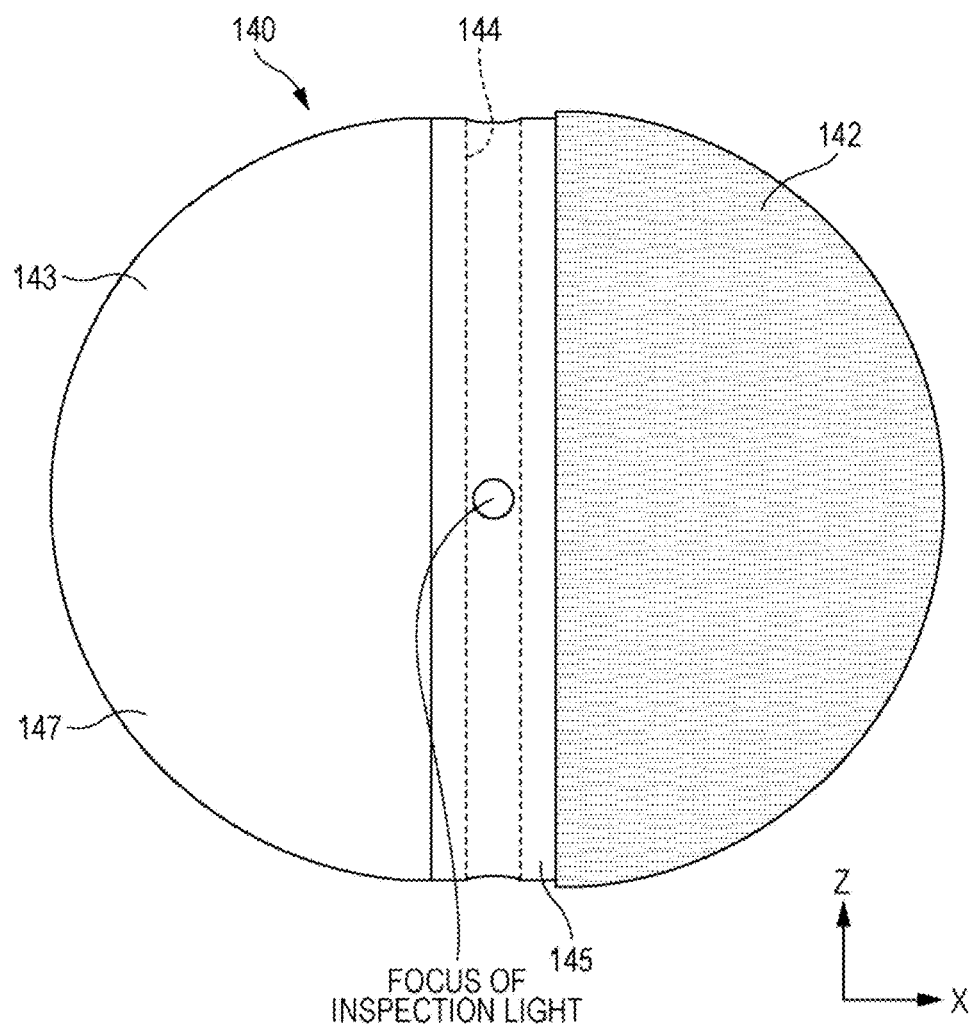
FIG. 12 is a side view of the flow cell according to the fourth embodiment of the present disclosure.
Figure 13:
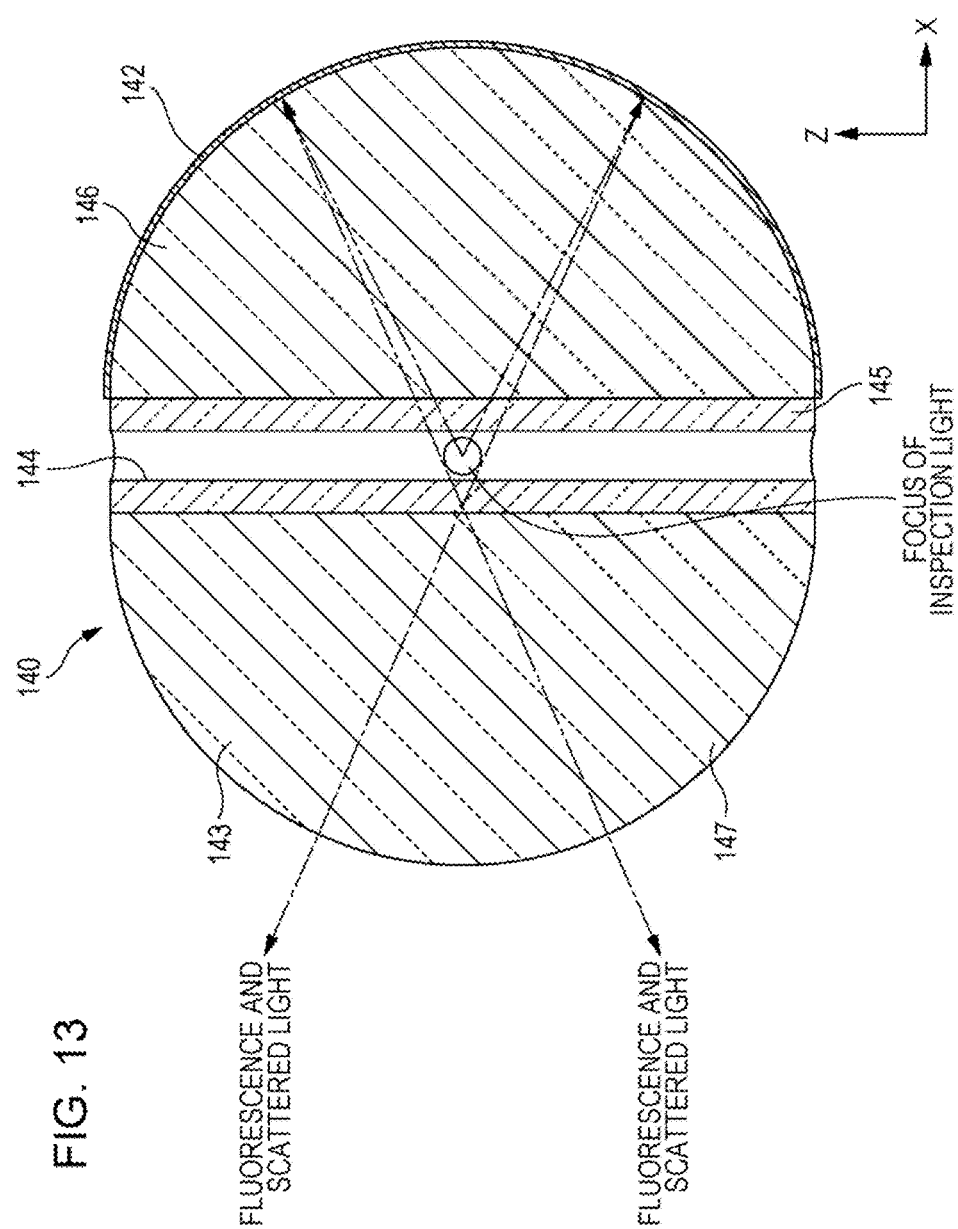
FIG. 13 is a sectional view of the flow cell according to the fourth embodiment of the present disclosure.

In a particle detector according to a fourth embodiment illustrated in FIG. 10, a flow cell 140 includes, as illustrated in FIG. 11, a plate-shaped member 145, a first semispherical member 146, and a second semispherical member 147. The plate-shaped member 145 is transparent and includes a first main surface 211, a second main surface 212 that faces the first main surface 211, and side surfaces 213 and 214 that are perpendicular to the first and second main surfaces 211 and 212. The plate-shaped member 145 has a through hole 144 penetrating therethrough from the side surface 213 to the side surface 214. The first semispherical member 146 is transparent and disposed on the first main surface 211 of the plate-shaped member 145. The second semispherical member 147 is transparent and disposed on the second main surface 212 of the plate-shaped member 145. As illustrated in FIGS. 11 to 13, in the flow cell 140, a semispherical reflective film 142 covers the first semispherical member 146, and the second semispherical member 147 functions as a semispherical lens portion 143.

The first main surface 211 and the second main surface 212 of the plate-shaped member 145 each have, for example, a rectangular shape. The shapes of the first main surface 211 and the second main surface 212 may conform to the shape of a holder of the flow cell. The through hole 144 is perpendicular to the side surfaces 213 and 214 of the plate-shaped member 145. The through hole 144 passes through, for example, the center of the plate-shaped member 145 which is the center of the flow cell 140. The through hole 144 has, for example, a circular sectional shape when seen in the extending direction thereof. The extending direction of the through hole 144 is perpendicular to the traveling direction of the inspection light and perpendicular to the major axis direction of the elliptical mirror 50 illustrated in FIG. 10.

The excitation light as the inspection light for detecting the particles flowing through the flow cell 140 is incident upon, for example, a side surface perpendicular to the side surfaces 213 and 214 of the plate-shaped member 145 toward the through hole 144. Preferably, the side surface of the plate-shaped member 145 irradiated with the excitation light are ground so as to have a high smoothness.

The first and second semispherical members 146 and 147 illustrated in FIG. 11 each have a bottom surface and a spherical surface. Outer diameters of the bottom surfaces of the first and second semispherical members 146 and 147 may be the same as or smaller than the widths of the first main surface 211 and the second main surface 212 of the plate-shaped member 145. The first and second semispherical members 146 and 147 can be two halves of a complete sphere. Alternatively, the first and second semispherical members 146 and 147 may be convex lens members the curvatures and the thicknesses of which are selected so that the reaction light generated at the intersection point of the inspection light and the through hole 144 is perpendicularly incident upon the surfaces of the first and second semispherical members 146 and 147.

The semispherical reflective film 142 that covers the first semispherical member 146 illustrated in FIGS. 11 to 13 is, for example, a vapor deposited film and formed of metal or the like. Alternatively, the semispherical reflective film 142 may be a dielectric multilayer film. Part of the second semispherical member 147 not covered by the semispherical reflective film 142 functions as the semispherical lens portion 143. The semispherical reflective film 142 and the semispherical lens portion 143 face each other.

As illustrated in FIG. 13, the fluorescence and the scattered light generated by fluorescent particles that are irradiated with the excitation light in the through hole 144 are omnidirectionally emitted from the fluorescent particles. Here, the fluorescence and the scattered light having traveled toward the semispherical lens portion 143 of the flow cell 140 exit through a surface of the semispherical lens portion 143 and reach the elliptical mirror 50. In the flow cell 140, when the thickness of the plate-shaped member 145 is less than the thickness of the semispherical lens portion 143, the shape of the flow cell 140 approximates a spherical shape. Thus, in the case where the focus of the inspection light is coincident with the center of the flow cell 140, the fluorescence and the scattered light generated at the focus of the inspection light are perpendicularly or substantially perpendicularly incident upon the surface of the semispherical lens portion 143. Thus, the fluorescence and the scattered light exit through the surface of the semispherical lens portion 143 without or substantially without being refracted at the surface of the semispherical lens portion 143.

The fluorescence and the scattered light having traveled toward the semispherical reflective film 142 of the flow cell 140 are reflected by the semispherical reflective film 142, exit through the surface of the semispherical lens portion 143, and reach the elliptical mirror 50. In the case where the shape of the flow cell 140 can approximate the spherical shape and the focus of the inspection light is coincident with the center of the flow cell 140, the fluorescence and the scattered light generated at the focus of the inspection light are perpendicularly or substantially perpendicularly incident upon the semispherical reflective film 142. Thus, the fluorescence and the scattered light are perpendicularly or substantially perpendicularly reflected by the semispherical reflective film 142, pass through the center or a portion near the center of the flow-cell 140, and exit through the surface of the semispherical lens portion 143 without or substantially without being refracted at the surface of the semispherical lens portion 143.

The light intensity of the inspection light passing through the plate-shaped member 145 is higher than the light intensities of the fluorescence and the scattered light generated by the particles in the through hole 144. The excitation light, which has a high light intensity, may cause the stray light. Thus, the plate-shaped member 145 upon which the inspection light is incident is preferably formed of a material having a high transparency such as synthetic quartz. In contrast, the fluorescence and the scattered light, which have low light intensities, are unlikely to cause the stray light. Thus, although the transparencies of the materials of the first and second semispherical members 146 and 147 may be the same as the transparency of the material of the plate-shaped member 145, the first and second semispherical members 146 and 147 may alternatively be formed of cheap materials having lower transparencies than the transparency of the material of the plate-shaped member 145 as long as the first and second semispherical members 146 and 147 allow the fluorescence and the scattered light to pass therethrough.

Specifically, the first and second semispherical members 146 and 147 may be formed of a silica glass. Alternatively, the first and second semispherical members 146 and 147 may be formed of different optical glass from silica glass or transparent resin such as polymethyl methacrylate (PMMA).

Other elements of the particle detector according to the fourth embodiment are the same as or similar to those of the first embodiment. Also with the particle detector according to the fourth embodiment, the reaction light such as fluorescence and scattered light generated in the flow cell 140 can be efficiently condensed and detected.

FIFTH EMBODIMENT

Figure 14:
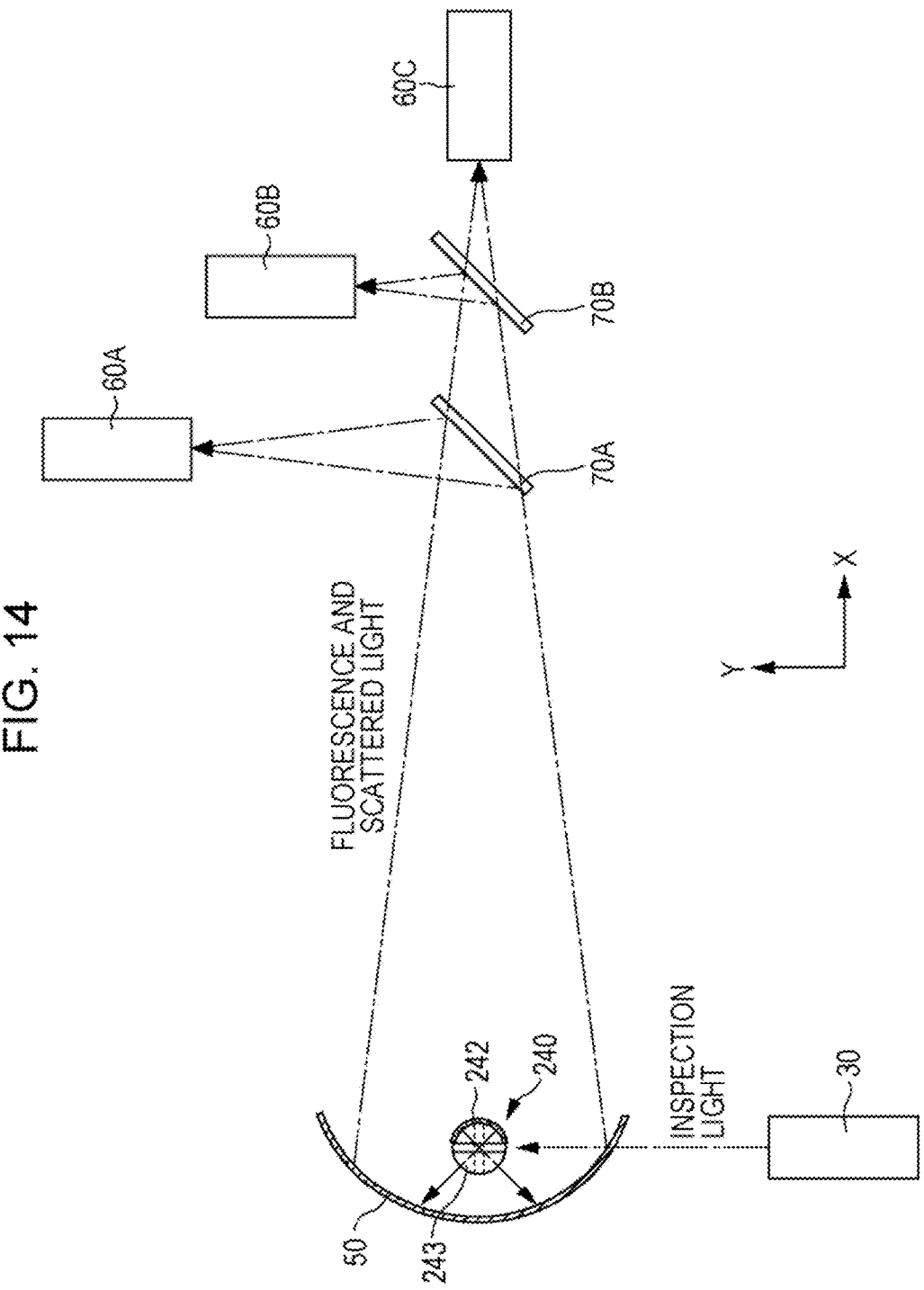
FIG. 14 is a schematic view of a particle detector according to a fifth embodiment of the present disclosure.
Figure 15:
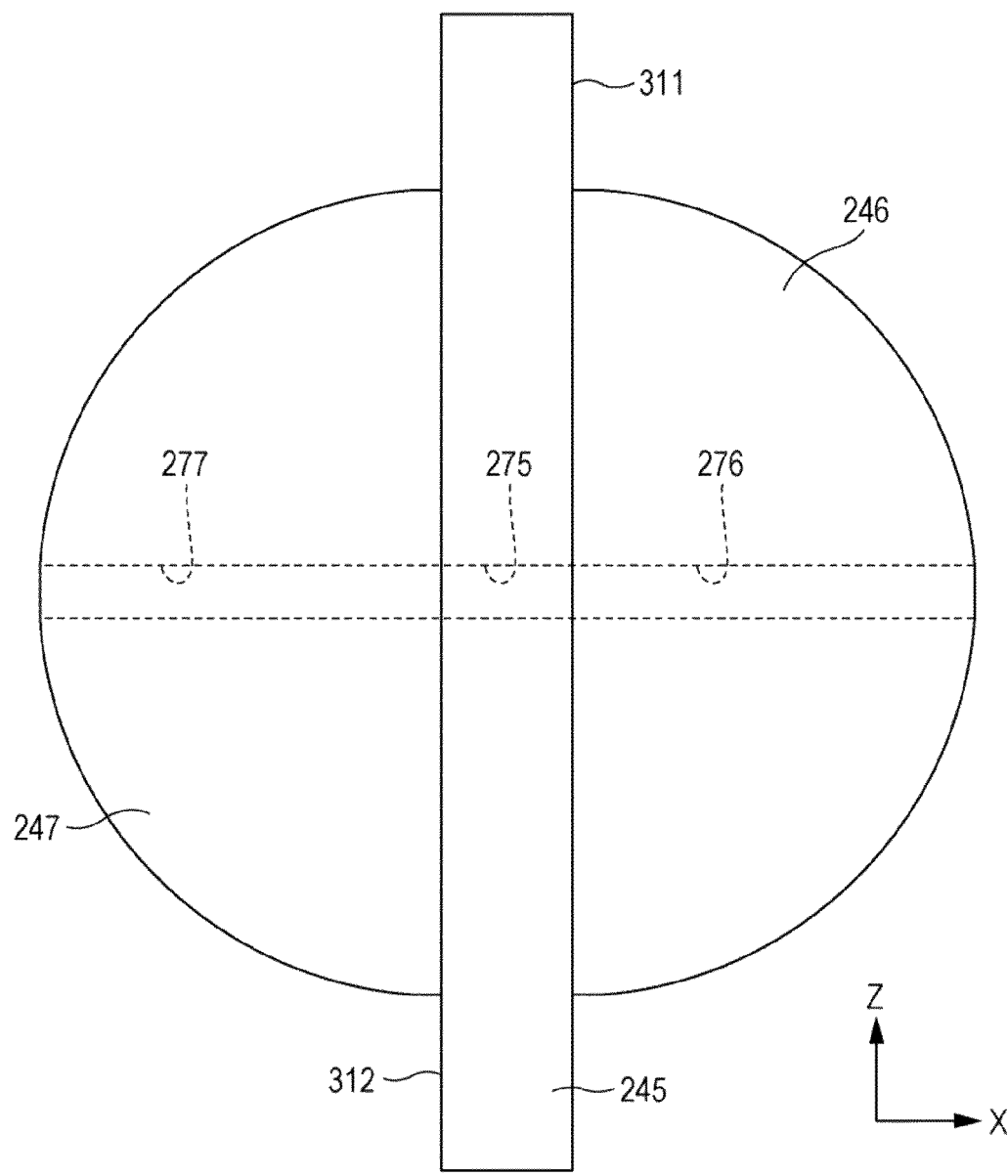
FIG. 15 is a schematic view of a plate-shaped member, a first semispherical member, and a second semispherical member which are included in a flow cell according to the fifth embodiment of the present disclosure.
Figure 16:
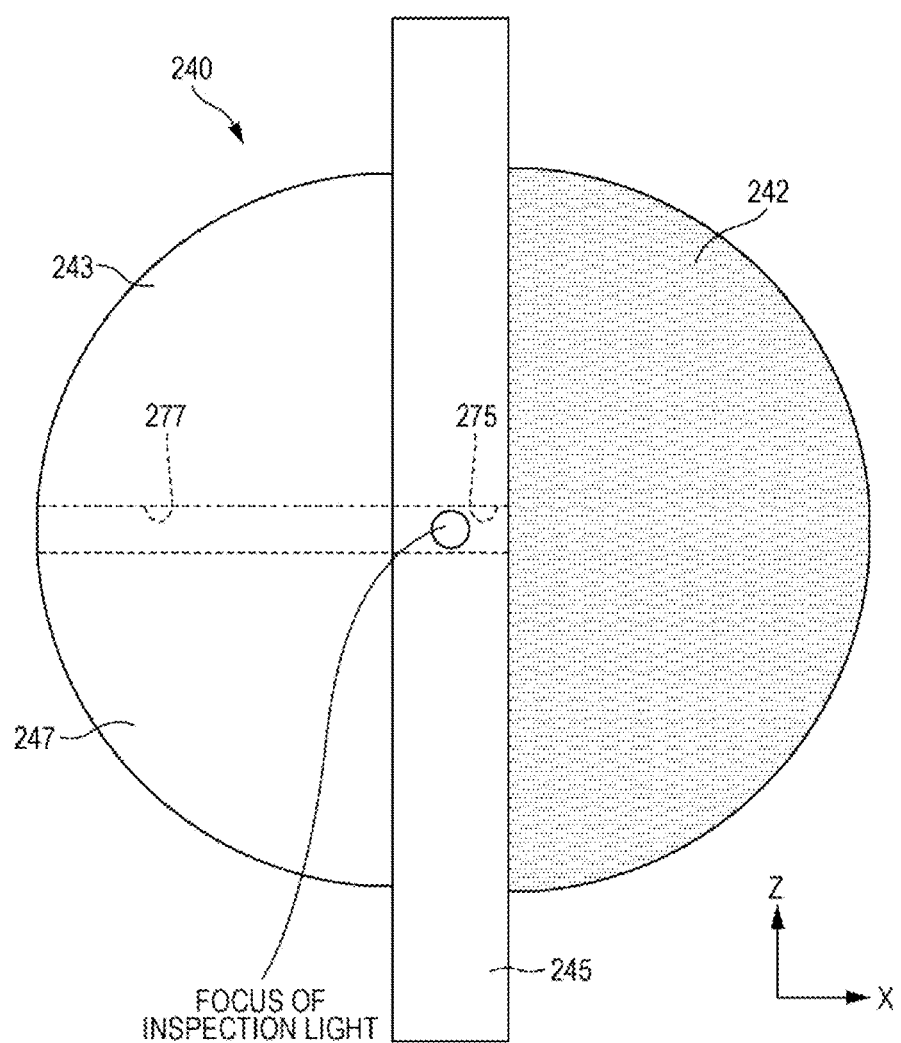
FIG. 16 is a side view of the flow cell according to the fifth embodiment of the present disclosure.
Figure 17:
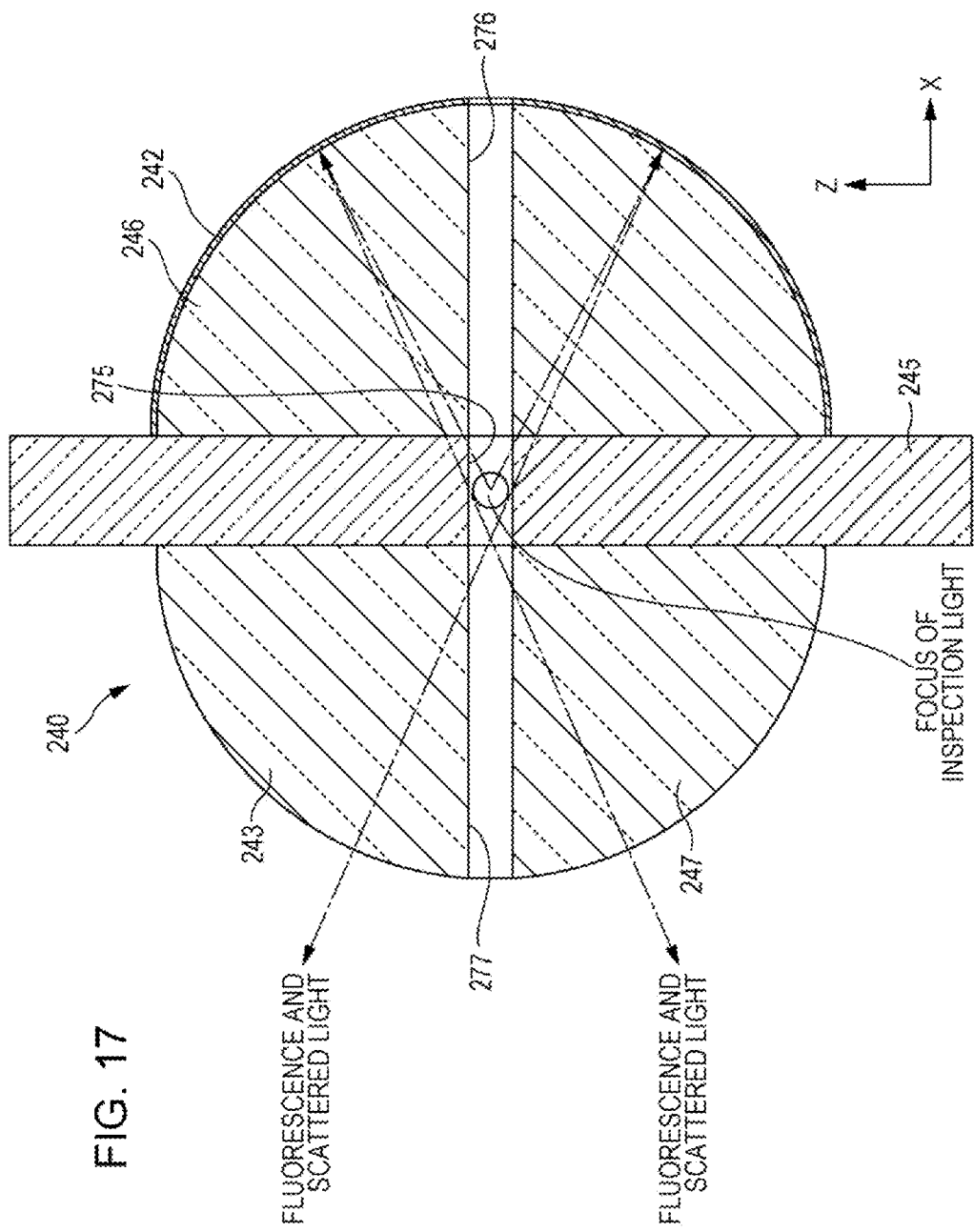
FIG. 17 is a sectional view of the flow cell according to the fifth embodiment of the present disclosure.
Figure 18:
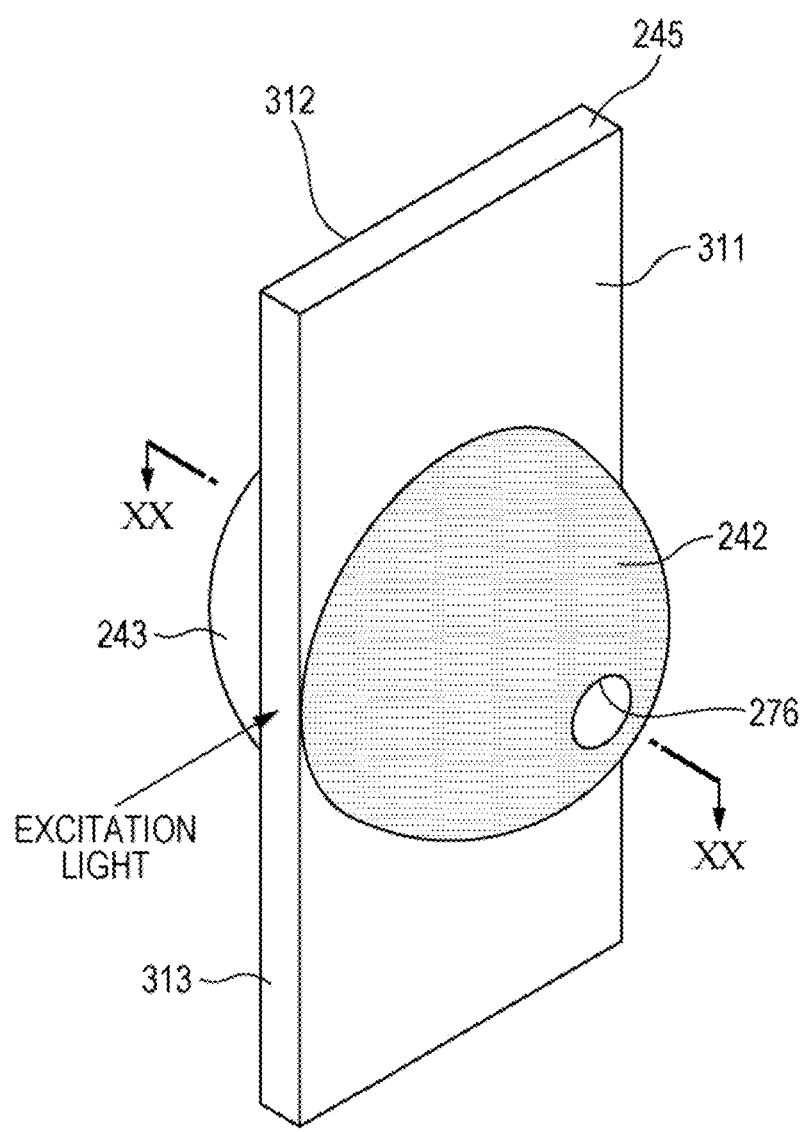
FIG. 18 is a schematic perspective view of the flow cell according to the fifth embodiment of the present disclosure.

A flow cell 240 of a particle detector according to a fifth embodiment illustrated in FIG. 14 includes, as illustrated in FIG. 15, a plate-shaped member 245, a first semispherical member 246, and a second semispherical member 247. The plate-shaped member 245 is transparent and includes a first main surface 311, a second main surface 312 that faces the first main surface 311, and has a through hole 275 penetrating therethrough from the first main surface 311 to the second main surface 312. The first semispherical member 246 is transparent, has a through hole 276, and is disposed on the first main surface 311 of the plate-shaped member 245 such that the through hole 275 of the plate-shaped member 245 and the through hole 276 of the first semispherical member 246 communicate with each other. The second semispherical member 247 is transparent, has a through hole 277, and is disposed on the second main surface 312 of the plate-shaped member 245 such that the through hole 275 of the plate-shaped member 245 and the through hole 277 of the second semispherical member 247 communicate with each other.

As illustrated in FIGS. 15 to 20, in the flow cell 240, a semispherical reflective film 242 covers the first semispherical member 246, and the second semispherical member 247 functions as a semispherical lens portion 243. The semispherical reflective film 242 that covers the first semispherical member 246 is, for example, a vapor deposited film and formed of metal or the like. Alternatively, the semispherical reflective film 242 may be a dielectric multilayer film. The semispherical reflective film 242 and the semispherical lens portion 243 face each other.

The first main surface 311 and the second main surface 312 of the plate-shaped member 245 each have, for example, a rectangular shape. The shapes of the first main surface 311 and the second main surface 312 may conform to the shape of a holder of the flow cell 240. The through hole 275 is perpendicular to the first and second main surfaces 311 and 312. The plate-shaped member 245 is formed of, for example, silica glass. Preferably, a side surface of the plate-shaped member 245 irradiated with the excitation light is ground so as to have a high smoothness.

The through hole 275 provided in the plate-shaped member 245 passes through, for example, the center of the plate-shaped member 245 which is the center of the flow cell 240. The through hole 275 has, for example, a circular sectional shape when seen in the extending direction thereof. The extending direction of the through hole 275 is perpendicular to the traveling direction of the inspection light and parallel to the major axis direction of the elliptical mirror 50.

The first and second semispherical members 246 and 247 each have a bottom surface and a spherical surface. Outer diameters of the bottom surfaces of the first and second semispherical members 246 and 247 may be the same as or smaller than the widths of the first main surface 311 and the second main surface 312 of the plate-shaped member 245. The through hole 276 of the first semispherical member 246 is perpendicularly provided from the top to the bottom of the first semispherical member 246. The through hole 276 has, for example, a circular sectional shape when seen in the extending direction thereof. The through hole 277 of the second semispherical member 247 is also perpendicularly provided from the top to the bottom of the second semispherical member 247. The through hole 277 has, for example, a circular sectional shape when seen in the extending direction thereof. The first and second semispherical members 246 and 247 are formed of, for example, silica glass. Alternatively, the first and second semispherical members 246 and 247 may be formed of, for example, different optical glass from silica glass or transparent resin such as PMMA.

The first and second semispherical members 246 and 247 can be two halves of a complete sphere. Alternatively, the first and second semispherical members 246 and 247 may be convex lens members the curvatures and the thicknesses of which are selected so that the reaction light generated at the intersection point of the inspection light and the through hole 275 is perpendicularly incident upon the surfaces of the first and second semispherical members 246 and 247.

In the flow cell 240, the fluid flows through the through hole 276 of the first semispherical member 246, the through hole 275 of the plate-shaped member 245, and the through hole 277 of the second semispherical member 247. The fluid may flow from the first semispherical member 246 side to the second semispherical member 247 side or from the second semispherical member 247 side to the first semispherical member 246 side.

The excitation light as the inspection light for detecting the particles flowing through the flow cell 240 is incident upon, for example, the side surface perpendicular to the first and second main surfaces 311 and 312 of the plate-shaped member 245 toward the through hole 275. The fluorescence and the scattered light generated by the fluorescent particles that are irradiated with the excitation light in the through hole 275 are omnidirectionally emitted from the fluorescent particles.

The fluorescence and the scattered light having traveled toward the semispherical lens portion 243 of the flow cell 240 exit through a surface of the semispherical lens portion 243 and reach the elliptical mirror 50. In the flow cell 240, when the thickness of the plate-shaped member 245 is less than the thickness of the semispherical lens portion 243, the shape of the flow cell 240 approximates a spherical shape. Thus, in the case where the focus of the inspection light is coincident with the center of the flow cell 240, the fluorescence and the scattered light generated at the focus of the inspection light are perpendicularly or substantially perpendicularly incident upon the surface of the semispherical lens portion 243. Thus, the fluorescence and the scattered light exit through the surface of the semispherical lens portion 243 without or substantially without being refracted at the surface of the semispherical lens portion 243.

The fluorescence and the scattered light having traveled toward the semispherical reflective film 242 of the flow cell 240 are reflected by the semispherical reflective film 242, exit through the surface of the semispherical lens portion 243, and reach the elliptical mirror 50. In the case where the shape of the flow cell 240 can approximate the spherical shape and the focus of the inspection light is coincident with the center of the flow cell 240, the fluorescence and the scattered light generated at the focus of the inspection light are perpendicularly or substantially perpendicularly incident upon the semispherical reflective film 242. Thus, the fluorescence and the scattered light are perpendicularly or substantially perpendicularly reflected by the semispherical reflective film 242, pass through the center or a portion near the center of the flow cell 240, and exit through the surface of the semispherical lens portion 243 without or substantially without being refracted at the surface of the semispherical lens portion 243.

Other elements of the particle detector according to the fifth embodiment are the same as or similar to those of the first or second embodiment. Also with the particle detector according to the fifth embodiment, the reaction light such as fluorescence and scattered light generated in the flow cell 240 can be efficiently condensed and detected.

The through holes 276 and 277 of the first and second semispherical members 246 and 247 are not irradiated with the excitation light. Accordingly, the smoothnesses of inner walls of the through holes 276 and 277 of the first and second semispherical members 246 and 247 may be the same as the smoothness of an inner wall of the through hole 275 of the plate-shaped member 245 or may be lower than the smoothness of the inner wall of the through hole 275 of the plate-shaped member 245.

Furthermore, as the diameter of the through hole 275 of the plate-shaped member 245 reduces, a region from the focus of the inspection light in which inspection object substances flows reduces and the likelihood of a plurality of inspection object substances simultaneously passing through the focus of the inspection light reduces. Thus, as the diameter of the through hole 275 reduces, resolution for detecting the fluorescence and the scattered light tends to be improved. In contrast, the diameters of the through holes 276 and 277 of the first and second semispherical members 246 and 247 not irradiated with the excitation light produce a small effect on the resolution for detecting the fluorescence and the scattered light. Accordingly, the diameters of the through holes 276 and 277 of the first and second semispherical members 246 and 247 may be the same as the diameter of the through hole 275 of the plate-shaped member 245 or may be larger than the diameter of the through hole 275 of the plate-shaped member 245.

Furthermore, the light intensity of the inspection light passing through the plate-shaped member 245 is higher than the light intensities of the fluorescence and the scattered light generated by the particles in the through hole 275. The excitation light, which has a high light intensity, may cause the stray light. Thus, the plate-shaped member 245 upon which the inspection light is incident is preferably formed of a material having a high transparency such as synthetic quartz. In contrast, the fluorescence and the scattered light, which have low light intensities, are unlikely to cause the stray light. Thus, although the transparencies of the materials of the first and second semispherical members 246 and 247 may be the same as the transparency of the material of the plate-shaped member 245, the first and second semispherical members 246 and 247 may alternatively be formed of cheap materials having lower transparencies than the transparency of the material of the plate-shaped member 245 as long as the first and second semispherical members 246 and 247 allow the fluorescence and the scattered light to pass therethrough.

Figure 21:
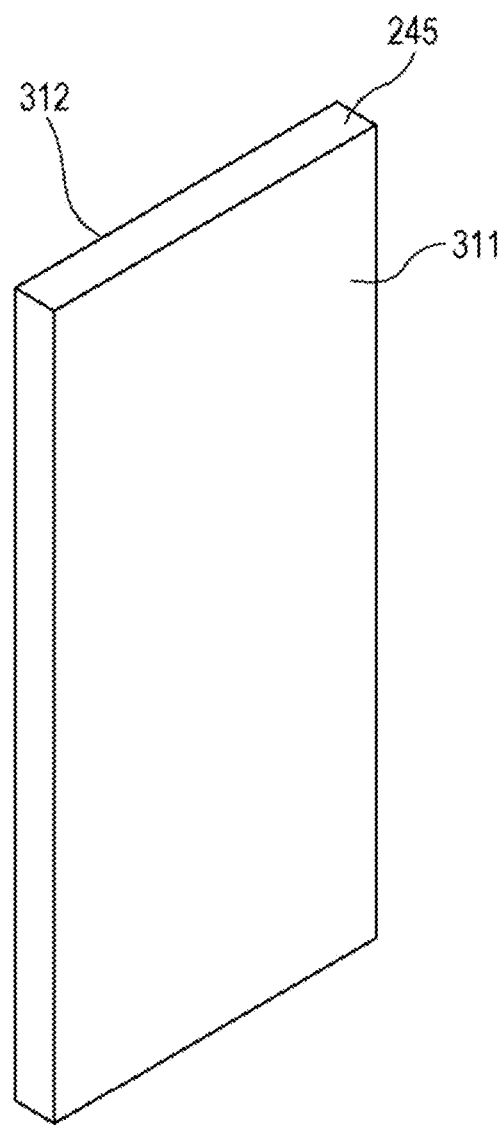
FIG. 21 is a view of a step illustrating a method of producing the flow cell according to the fifth embodiment of the present disclosure.
Figure 22:
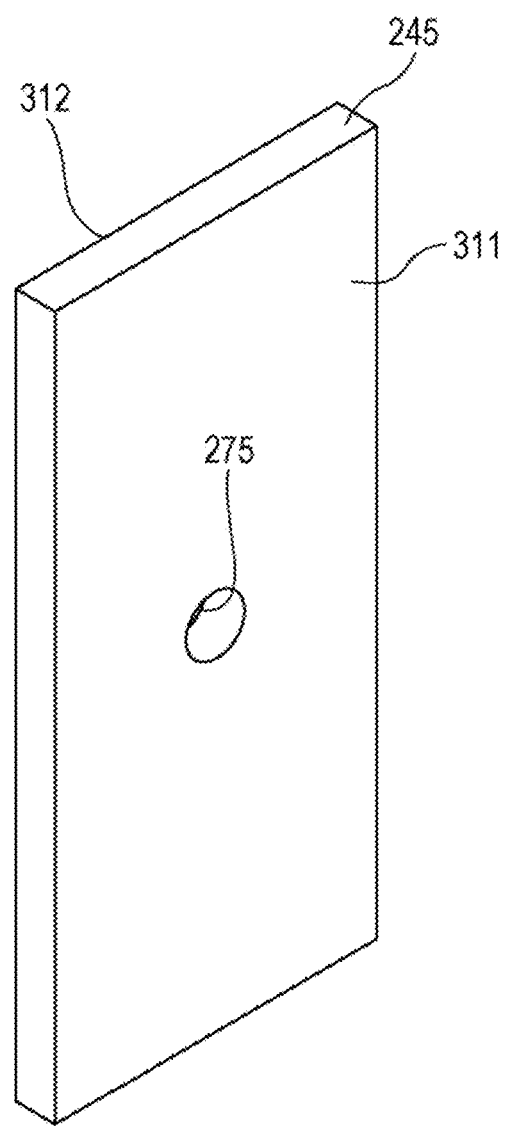
FIG. 22 is a view of a step illustrating the method of producing the flow cell according to the fifth embodiment of the present disclosure.
Figure 23:
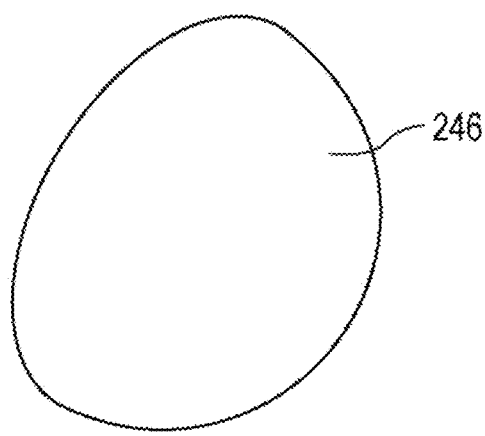
FIG. 23 is a view of a step illustrating the method of producing the flow cell according to the fifth embodiment of the present disclosure.
Figure 24:
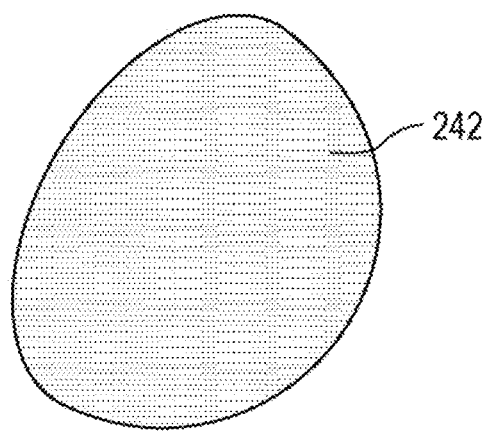
FIG. 24 is a view of a step illustrating the method of producing the flow cell according to the fifth embodiment of the present disclosure.
Figure 25:
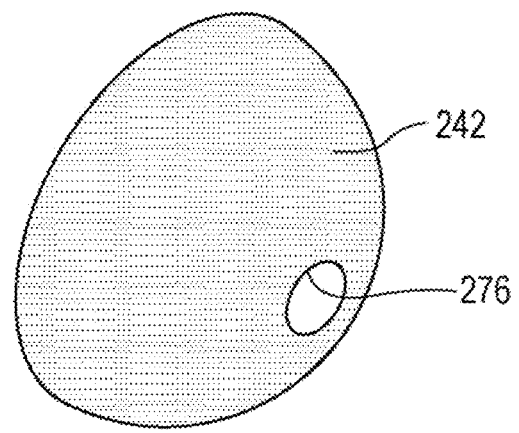
FIG. 25 is a view of a step illustrating the method of producing the flow cell according to the fifth embodiment of the present disclosure.
Figure 26:
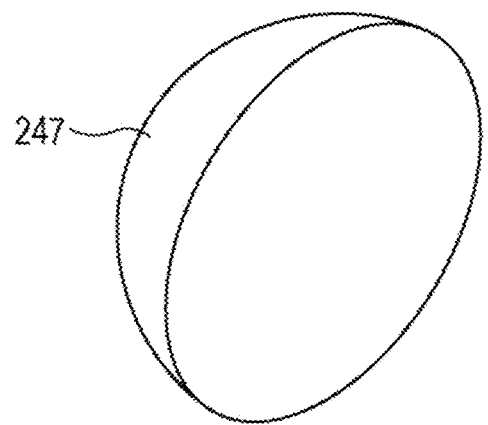
FIG. 26 is a view of a step illustrating the method of producing the flow cell according to the fifth embodiment of the present disclosure.
Figure 27:
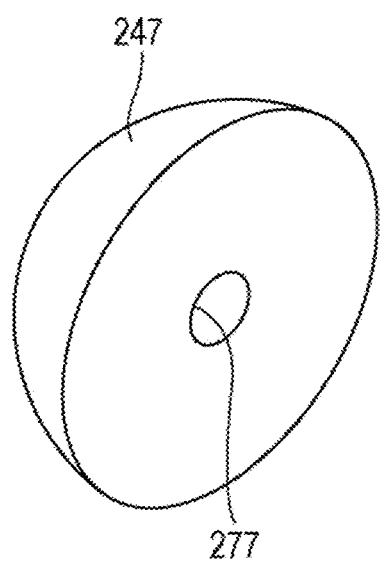
FIG. 27 is a view of a step illustrating the method of producing the flow cell according to the fifth embodiment of the present disclosure.

Next, a method of producing the flow cell 240 according to the fifth embodiment is described. The plate-shaped member 245 is prepared as illustrated in FIG. 21, and the through hole 275 is provided in the plate-shaped member 245 as illustrated in FIG. 22. Furthermore, the first semispherical member 246 is prepared as illustrated in FIG. 23, and the semispherical reflective film 242 is formed on the semispherical surface of the first semispherical member 246 as illustrated in FIG. 24. Furthermore, as illustrated in FIG. 25, the through hole 276 is provided in the first semispherical member 246 on which the semispherical reflective film 242 has been provided. Furthermore, the second semispherical member 247 is prepared as illustrated in FIG. 26, and the through hole 277 is provided in the second semispherical member 247 as illustrated in FIG. 27.

The through holes 275, 276, and 277 can be provided by, for example, etching. Alternatively, the through holes 275, 276, and 277 may be provided by drilling. Furthermore, after the through holes 275, 276, and 277 have been formed, the inner walls of the through holes 275, 276, and 277 may be, for example, ground so as to improve the smoothnesses of the inner walls of the through holes 275, 276 and 277. Alternatively, the inner wall of only the through hole 275 may be, for example, ground so as to improve the smoothness of the inner wall of the through hole 275.

Here, a through hole having a highly smooth inner wall can be easily provided in the plate-shaped member than in the semispherical members. Furthermore, as has been described, in the flow cell 240 to be produced, the plate-shaped member 245 is irradiated with the excitation light and the first and second semispherical members 246 and 247 are not irradiated with the excitation light. Accordingly, the production cost of the flow cell 240 according to the fifth embodiment may be reduced by providing the through hole 275 having a highly smooth inner wall in the plate-shaped member 245, and providing the through holes 276 and 277 having inner walls having lower smoothnesses than the smoothness of the inner wall of the through hole 275 in the first and second semispherical members 246 and 247.

Furthermore, a through hole having a small diameter can be easily provided in the plate-shaped member than in the semispherical members. Furthermore, as has been described, as the diameter of the through hole 275 of the plate-shaped member 245 reduces, the resolution for detecting the fluorescence and the scattered light is improved with the flow cell 240 to be produced. However, the diameters of the through holes 276 and 277 of the first and second semispherical members 246 and 247 not irradiated with the excitation light produce a small effect on the resolution for detecting the fluorescence and the scattered light. Accordingly, the production cost of the flow cell 240 according to the fifth embodiment may be reduced by providing the through hole 275 having a small diameter in the plate-shaped member 245, and providing the through holes 276 and 277 having larger diameters than the diameter of the through hole 275 in the first and second semispherical members 246 and 247.

Figure 28:
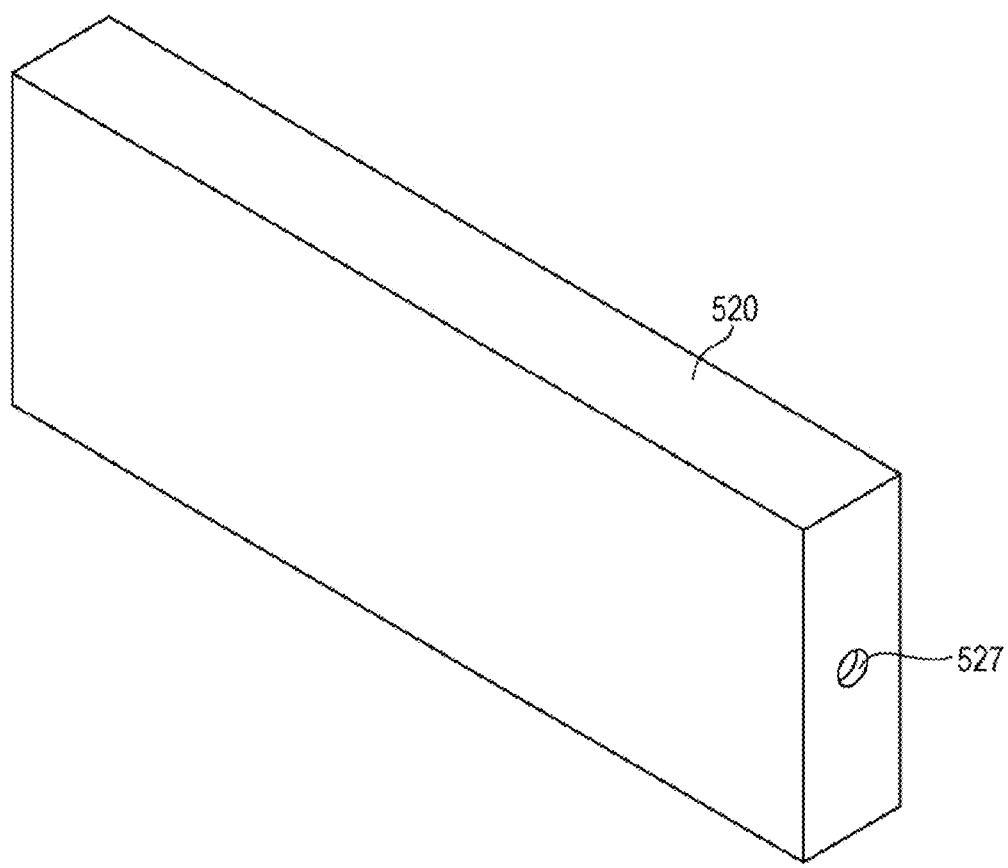
FIG. 28 is a view of a step illustrating the method of producing the flow cell according to the fifth embodiment of the present disclosure.

The plate-shaped member 245 having the through hole 275 may be produced by a drawing method. For example, a glass base material 520 having a through hole 527 having a circular section as illustrated in FIG. 28 is prepared. The glass base material 520 is heated and drawn in the same direction as the extending direction of the through hole 527. Thus, the size of the glass base material 520 is reduced in section, and the diameter of the through hole 527 becomes equal to that of the through hole 275 of the plate-shaped member 245 to be produced illustrated in FIG. 22. After that, the plate-shaped member 245 illustrated in FIG. 22 is cut from an end portion of the glass base material 520 illustrated in FIG. 28. The plate-shaped member 245 having been cut may be ground.

Figure 19:
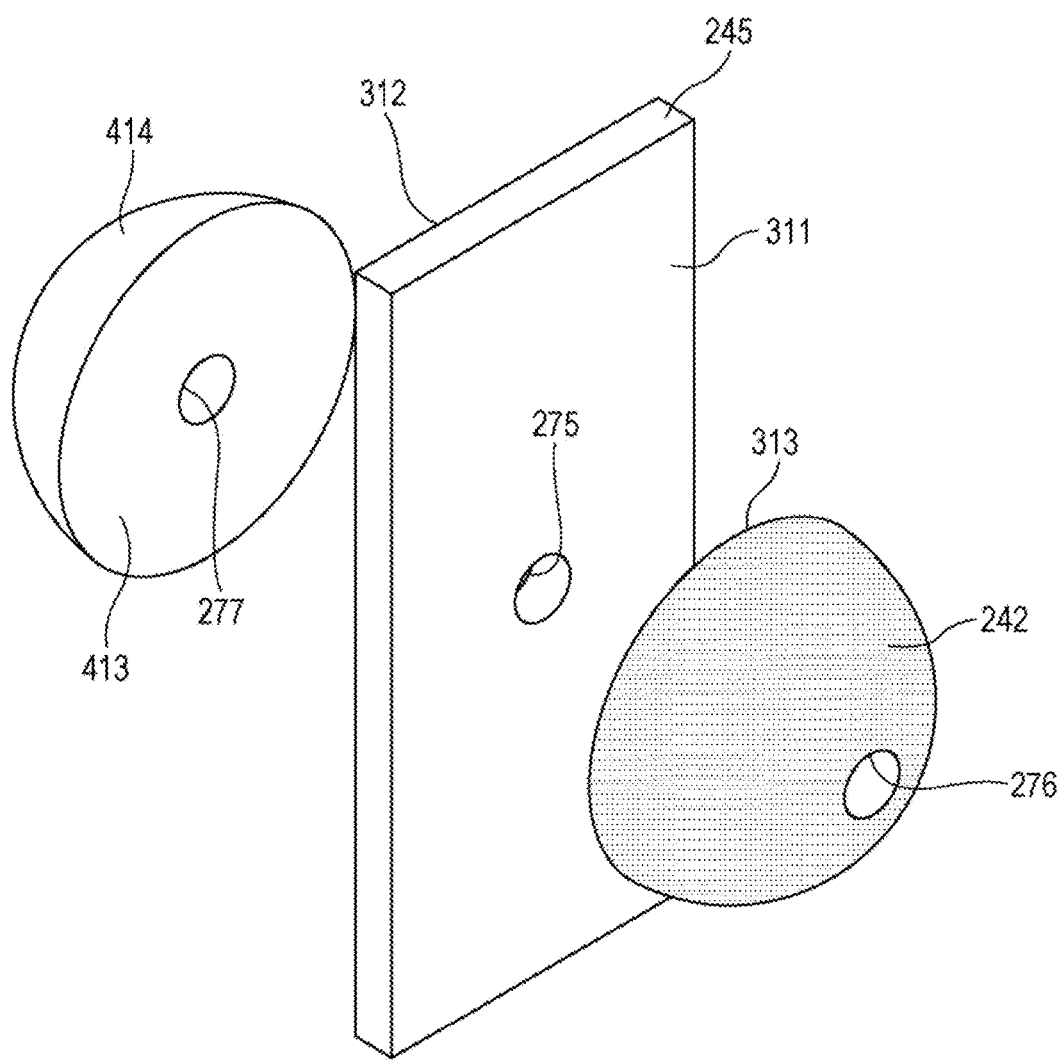
FIG. 19 is an exploded view of the flow cell according to the fifth embodiment of the present disclosure.
Figure 20:
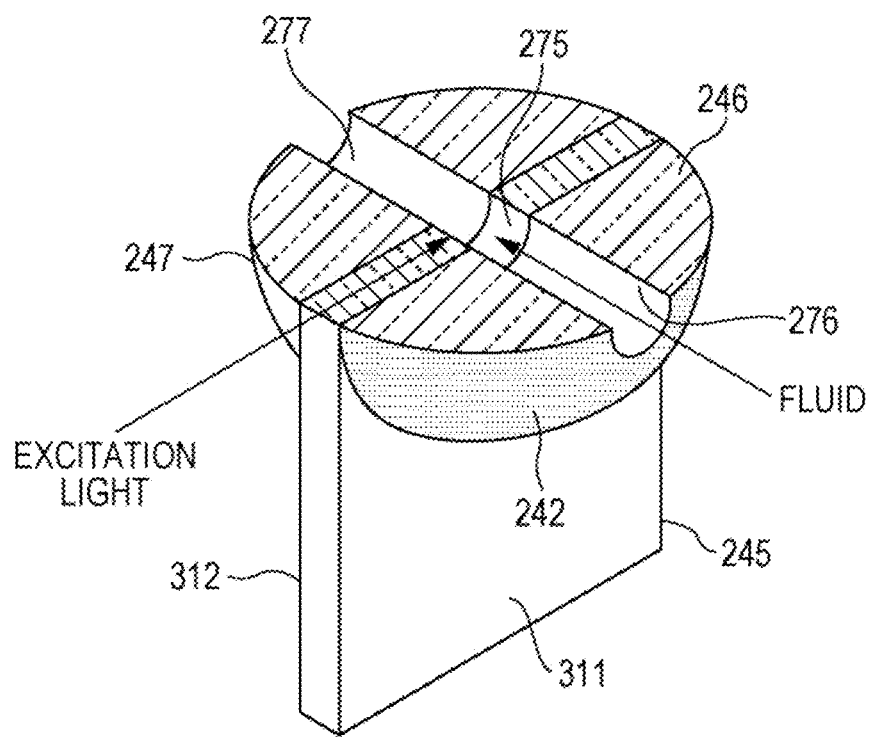
FIG. 20 is a schematic sectional view of the flow cell according to the fifth embodiment of the present disclosure seen in a XX-XX direction indicated in FIG. 18.

The plate-shaped member 245 and the first and second semispherical members 246 and 247 illustrated in FIG. 19 are positioned so as to allow the through holes 275, 276, and 277 to communicate with one another and are joined to one another by, for example, optical contact. Alternatively, the plate-shaped member 245 and the first and second semispherical members 246 and 247 may be bonded to one another with an optical adhesive or the like. Thus, the flow cell 240 according to the fifth embodiment is obtained.

With the above-described method of producing the flow cell 240 according to the fifth embodiment, by attaching the plate-shaped member 245 and the first and second semispherical members 246 and 247 to one another, the spatially shaped flow cell including the lens portion that is difficult to be integrally formed by molding can be produced.

Furthermore, when it is attempted that a through hole having corners between inner walls is provided in a member, cracking and formation of gaps tend to occur at the corners. In contrast, with the method of producing the flow cell 240 according to the fifth embodiment, the through holes 275, 276, and 277 having circular sectional shapes are formed. Thus, the occurrences of cracking and the formation of the gaps in the inner walls of the through holes 275, 276, and 277 can be suppressed.

Furthermore, difficulty in providing a through hole having a highly smooth inner wall in a member increases as the diameter of the through hole reduces and as the thickness of the member increases. Thus, it is difficult to improve the smoothness of the inner wall by, for example, grinding the inner wall of a through hole of a small diameter provided in the base material of the flow cell after the base material of the flow cell has been integrally formed. In contrast, with the above-described method of producing the flow cell 240 according to the fifth embodiment, by attaching to one another the plate-shaped member 245 and the first and second semispherical members 246 and 247 in which the through holes 275, 276, and 277 have been provided in advance, the diameter of the through hole 275 irradiated with the excitation light can be reduced and the smoothness of the inner wall of the through hole 275 irradiated with the excitation light can be improved.

Variant of Fifth Embodiment

Figure 29:
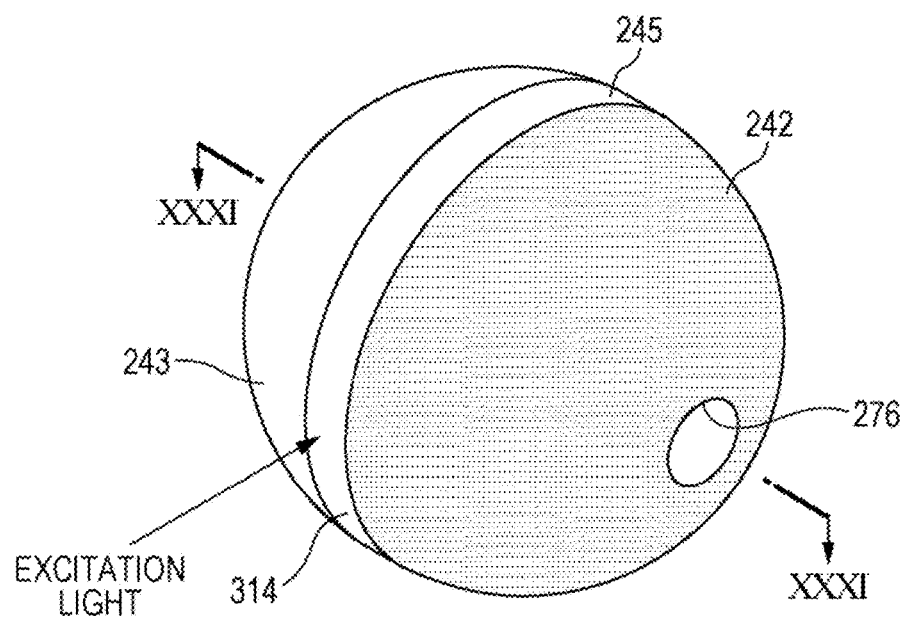
FIG. 29 is a schematic perspective view of a flow cell according to a variant of the fifth embodiment of the present disclosure.
Figure 30:
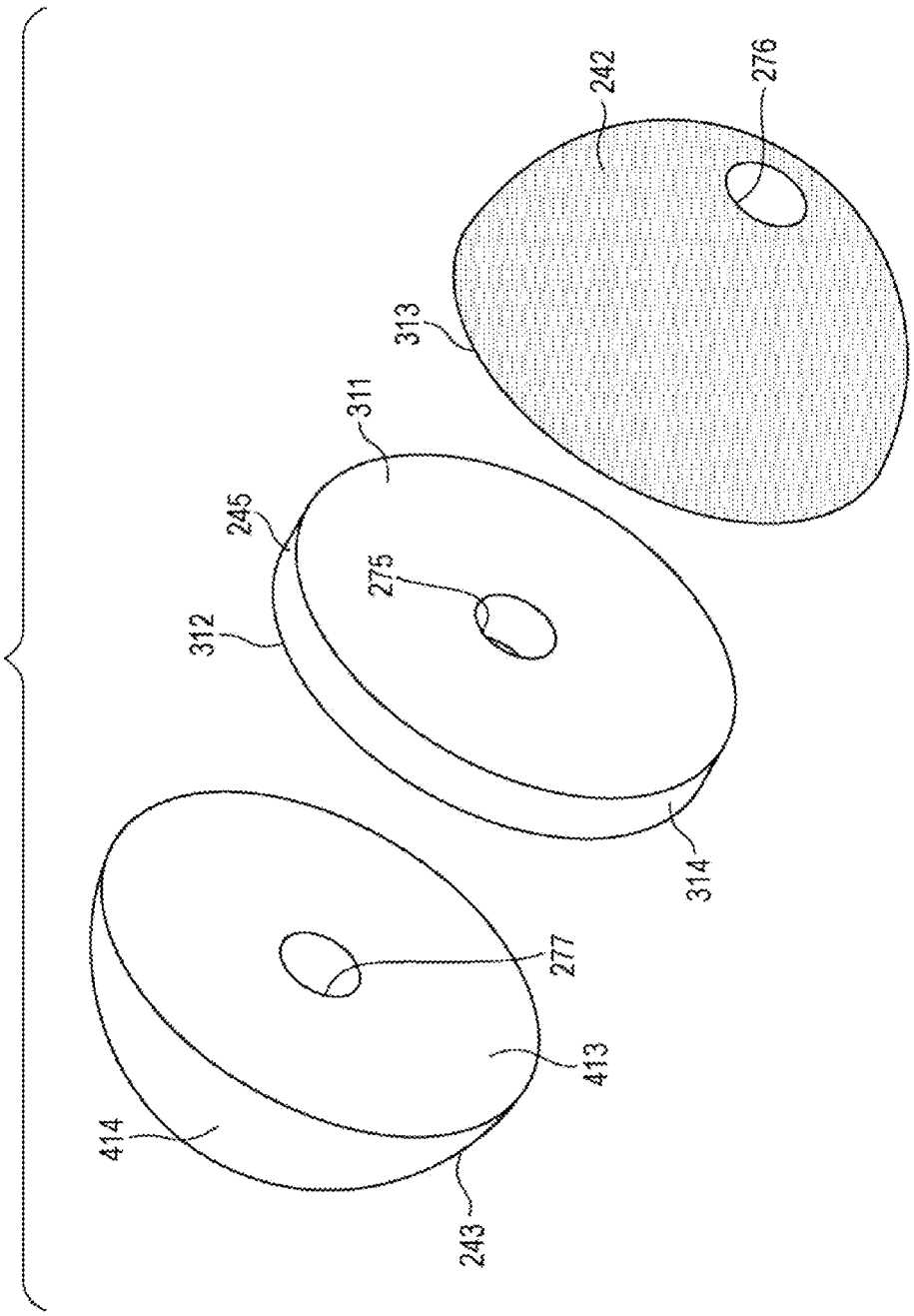
FIG. 30 is an exploded view of the flow cell according to the variant of the fifth embodiment of the present disclosure.
Figure 31:
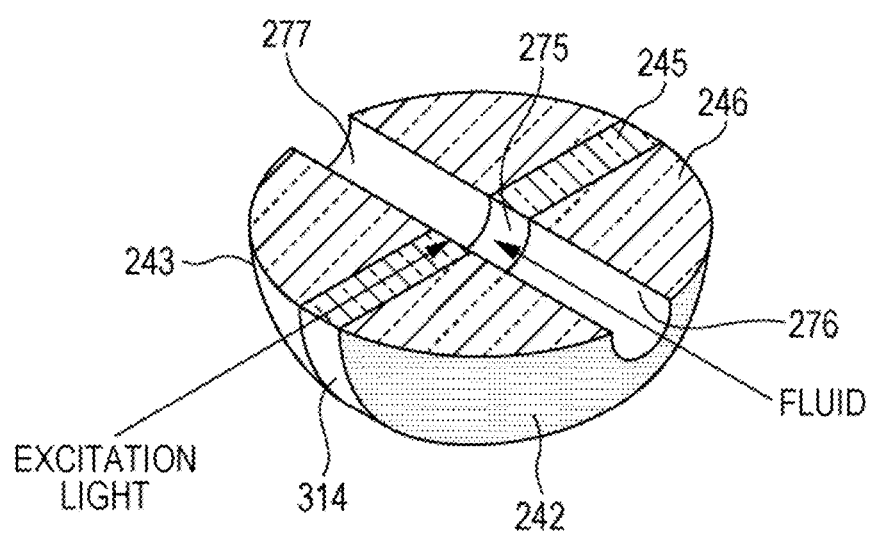
FIG. 31 is a schematic sectional view of the flow cell according to the variant of the fifth embodiment of the present disclosure seen in a XXXI-XXXI direction indicated in FIG. 29.

According to a variant of the fifth embodiment of the present disclosure, as illustrated in FIGS. 29 to 31, the first main surface 311 and the second main surface 312 of the plate-shaped member 245 of the flow cell each have a circular shape. Accordingly, the side surface 314 of the plate-shaped member 245 has an annular shape. The outer diameters of the first main surface 311 and the second main surface 312 of the plate-shaped member 245 may be larger than or the same as the outer diameters of the bottom surfaces 313 and 413 of the first and second semispherical members 246 and 247. Other elements of the flow cell according to the variant of the fifth embodiment are the same as or similar to those of the fifth embodiment.

Figure 32:
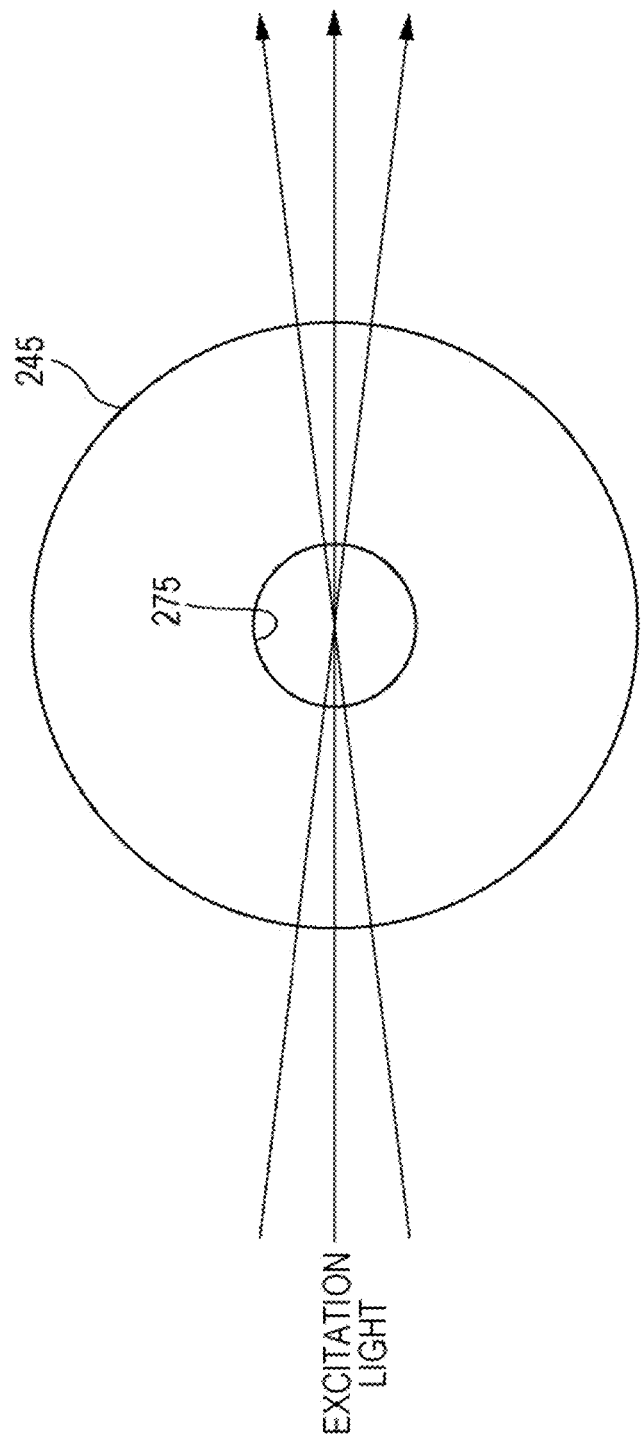
FIG. 32 is a schematic sectional view of the flow cell according to the variant of the fifth embodiment of the present disclosure.

In the case where an outer circumferential shape of the plate-shaped member 245 and the sectional shape of the through hole 275 are circular, by radiating the excitation light so as to be focused on the center of the through hole 275, the excitation light, is perpendicularly incident, upon the side surface 314 and the inner wall of the through hole 275 of the plate-shaped member 245 as illustrated in FIG. 32. Thus, the excitation light can be focused in the through hole 275 without being affected by the refractive index of the plate-shaped member 245.

OTHER EMBODIMENTS

Although the present disclosure has been described with the embodiments as described above, it should be understood that the description and the drawings serving as part of the present disclosure do not limit the present disclosure. One skilled in the art should clearly understand a variety of alternative embodiments, examples, and operational techniques from this disclosure. For example, the particle detector may detect only fluorescence emitted from the particles or detect only scattered light generated by the particles. It should be understood that, as described above, the present disclosure includes a variety of embodiments and the like that are not described herein.

The invention claimed is:

1. A particle detector, comprising:
an inspection light source configured to irradiate a flow cell with inspection light;
the flow cell configured to
allow a fluid containing a particle to flow therethrough, the flow cell including a semispherical reflective film configured to reflect reaction light generated by the particle irradiated with the inspection light, and a semispherical lens portion through which the reaction light reflected by the semispherical reflective film passes;
an elliptical mirror that has a first focus at a position of the flow cell, and that is configured to reflect the reaction light having passed through the semispherical lens portion of the flow cell; and
an optical detector disposed at a second focus of the elliptical mirror, the optical detector being configured to detect the reaction light reflected by the elliptical mirror.

2. The particle detector according to claim 1,
wherein the reaction light is fluorescence, scattered light, or a combination of the fluorescence and the scattered light.

3. The particle detector according to claim 1,
wherein the flow cell further includes a spherical member that is transparent and that has a through hole through which the fluid flows,
wherein the semispherical reflective film covers part of the spherical member, and
wherein a part of the spherical member not covered by the semispherical reflective film functions as the semispherical lens portion.

4. The particle detector according to claim 3, wherein a sectional shape of the through hole provided in the spherical member is circular.

5. The particle detector according to claim 1, wherein the elliptical mirror has a cut in a traveling direction of the inspection light.

6. The particle detector according to claim 1, wherein the semispherical reflective film has a cut in a traveling direction of the inspection light.

7. The particle detector according to claim 1, further comprising a stray light absorbing member configured to block or attenuate stray light, the stray light absorbing member being disposed in a traveling direction of the inspection light.

8. The particle detector according to claim 1,
wherein the flow cell includes a through hole through which the fluid flows, and
wherein an extending direction of the through hole is perpendicular to a traveling direction of the inspection light and perpendicular to a major axis direction of the elliptical mirror.

9. The particle detector according to claim 1,
wherein the flow cell is disposed such that a convex portion of the semispherical lens portion and a concave portion of the semispherical reflective film face the elliptical mirror.

10. The particle detector according to claim 1, further comprising a wavelength-selective reflector configured to wavelength-selectively reflect the reaction light reflected by the elliptical mirror, the wavelength-selective reflector being disposed between the first focus and the second focus of the elliptical mirror.

* * * * *